(12) United States Patent
Nakamura et al.

(10) Patent No.: US 9,297,930 B2
(45) Date of Patent: Mar. 29, 2016

(54) LOW WATER CONTENT SOFT LENS FOR EYE, AND METHOD FOR PRODUCING THE SAME

(71) Applicant: Toray Industries, Inc., Tokyo (JP)

(72) Inventors: Masataka Nakamura, Otsu (JP); Rumiko Kitagawa, Otsu (JP); Tsutomu Goshima, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 14/594,515

(22) Filed: Jan. 12, 2015

(65) Prior Publication Data

US 2015/0177417 A1 Jun. 25, 2015

Related U.S. Application Data

(63) Continuation of application No. 13/579,145, filed as application No. PCT/JP2011/053195 on Feb. 16, 2011, now Pat. No. 9,046,644.

(30) Foreign Application Priority Data

Feb. 16, 2010 (JP) .................................. 2010-030923

(51) Int. Cl.
*G02B 1/04* (2006.01)
*G02B 1/10* (2015.01)
*C08F 290/06* (2006.01)
*G02C 7/04* (2006.01)
*A61F 2/14* (2006.01)

(52) U.S. Cl.
CPC ............ *G02B 1/043* (2013.01); *C08F 290/068* (2013.01); *G02B 1/10* (2013.01); *G02C 7/04* (2013.01); *G02C 7/049* (2013.01); *A61F 2/14* (2013.01); *A61F 2240/001* (2013.01); *G02C 2202/16* (2013.01)

(58) Field of Classification Search
None
See application file for complete search history.

(56) References Cited

U.S. PATENT DOCUMENTS

| | | | |
|---|---|---|---|
| 4,954,586 A * | 9/1990 | Toyoshima et al. | ............ 526/245 |
| 6,043,328 A | 3/2000 | Domschke | |
| 6,451,871 B1 | 9/2002 | Winterton | |
| 8,044,112 B2 | 10/2011 | Matsuzawa | |
| 2003/0134132 A1 | 7/2003 | Winterton | |

FOREIGN PATENT DOCUMENTS

| | | |
|---|---|---|
| EP | 1539263 | 6/2005 |
| EP | 2122390 | 11/2009 |
| JP | 54024047 | 2/1979 |
| JP | 54081363 | 6/1979 |
| JP | 56051715 | 5/1981 |
| JP | 59229524 | 12/1984 |
| JP | 2188717 | 7/1990 |
| JP | 4318010 | 11/1992 |
| JP | 5005861 | 1/1993 |
| JP | 2002501211 | 1/2002 |
| JP | 2002047365 | 2/2002 |
| JP | 2005538418 | 12/2005 |
| JP | 2009540369 | 11/2009 |
| WO | 9631792 | 10/1996 |
| WO | 0157118 | 8/2001 |
| WO | 0192924 | 12/2001 |
| WO | 0216974 | 2/2002 |
| WO | 03057270 | 7/2003 |

OTHER PUBLICATIONS

European Search Report dated Aug. 14, 2014, application No. EP 11 74 4642.
Written Opinion and Search Report dated Mar. 7, 2014, application No. 2012061313.
Brian Chou, OD, FAAO: "The Evolution of Silicone Hydrogel Lenses", Contact Lens Spectrum, Jun. 1, 2008.
International Search Report dated Mar. 15, 2011, application No. PCT/JP2011/053195.
Entire patent prosecution history of U.S. Appl. No. 13/579,145, filed Aug. 15, 2012, entitled, "Low Water Content Soft Lens for Eye, and Method for Producing the Same."

* cited by examiner

*Primary Examiner* — Marc Zimmer
(74) *Attorney, Agent, or Firm* — RatnerPrestia

(57) ABSTRACT

A low water content soft lens for eye is provided, which includes a layer made of an acidic polymer and a basic polymer on at least a part of a surface of a base material containing a polysiloxane compound. Adhesion of the lens to the cornea during wear, which has hitherto been regarded as a problem in a conventional low water content soft lens for eye, can be reduced or avoided when using the low water content soft lens.

16 Claims, 1 Drawing Sheet

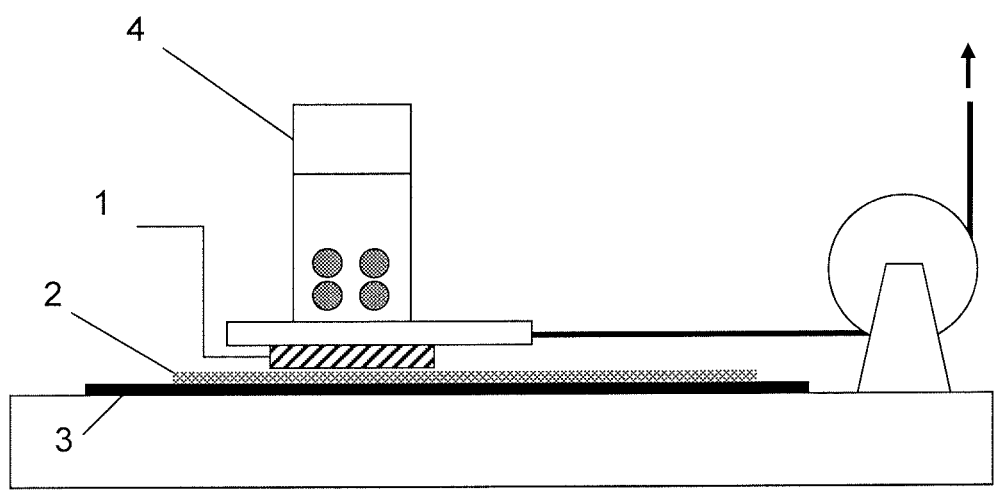

LOW WATER CONTENT SOFT LENS FOR EYE, AND METHOD FOR PRODUCING THE SAME

CROSS REFERENCE TO RELATED APPLICATIONS

This application is a continuation application of U.S. patent application Ser. No. 13/579,145, filed Aug. 15, 2012, which is a the U.S. National Phase application of PCT International Application No. PCT/JP2011/053195, filed Feb. 16, 2011, and claims priority to Japanese Patent Application No. 2010-030923, filed Feb. 16, 2010, the disclosures of each of these applications being incorporated herein by reference in their entireties for all purposes.

FIELD OF THE INVENTION

The present invention relates to a low water content soft lens for eye and a method for producing the same.

BACKGROUND OF THE INVENTION

Typical examples of a commercially available soft lens for eye include a soft contact lens. A hydrogel material having a water content of about 25 to 80% is commonly used in the commercially available soft contact lens. However, since the low water content soft contact lens made of the hydrogel material contains water, there arises a phenomenon in which water is vaporized from the contact lens. Thereby, certain fixed proportions of contact lens wearers feel dry more strongly as compared with the case of the naked eye, and thus feel uncomfortable. Among these contact lens wearers, some persons complain about a condition of so-called contact lens-related dry eye. Since a water-containing soft contact lens made of a hydrogel material is likely to be contaminated with components in a lacrimal fluid and also contains a large amount of water, there was also a risk of the growth of bacteria.

There has been known as, a highly oxygen permeable low water content soft contact lens, for example, a silicone rubber lens obtained by a method of adding a platinum-based catalyst to a mixture of polydimethylsiloxane in which both ends of the molecular chain are blocked with a vinylmethylsilyl group, and methyl hydrogen polysiloxane, followed by heat-curing using a molding method (Patent Literature 1). Patent Literatures 2 to 6 disclose a highly oxygen permeable contact lens material composed mainly of polysiloxane having a plurality of polymerizable functional groups.

Patent Literature 6 discloses a contact lens material made of a polymer obtained by polymerizing a difunctional organosiloxane macromer alone, or a polymer obtained by copolymerizing a difunctional organosiloxane macromer with the other monomers, and also discloses, as a monomer to be used in copolymerization, an acrylic acid fluoroalkyl ester or a methacrylic acid fluoroalkyl ester, and an acrylic acid alkyl ester or a methacrylic acid alkyl ester.

However, the following problems also lie in a conventional highly oxygen permeable low water content soft contact lens. First, a silicone rubber lens has such a drawback that a hydrophilized layer formed so as to improve hydrophobicity of the surface of the lens is peeled, or adhesion of the lens to the cornea occurs due to too large resilience, and thus the silicone rubber lens had not widely been put into practice.

A material composed mainly of polysiloxane having a plurality of polymerizable functional groups has high oxygen permeability and also has flexibility, and the material is considered to be one of materials which are suitable for a contact lens. However, since tackiness is left on the surface of the lens after polymerization, the lens may adhere to the cornea and is also insufficient in balance between flexibility of the lens and mechanical properties such as folding resistance.

There have been known various methods for modification of a surface of a soft lens for eye. Among these methods, there is known a method in which layers of two or more kinds of polymer materials are coated and accumulated in a layer by layer fashion (Patent Literatures 7 to 9). Among these methods, a method of alternately forming layers made of two polymer materials, each having an opposite electric charge, in a layer by layer fashion by coating is called an LbL method, and it is considered that each layer of the material is noncovalently bonded to the other layer made of a different material. However, the highly oxygen permeable soft lens for eye in which utility of this method is clearly shown is made only of a silicone hydrogel material, and utility to the low water content soft lens for eye has not been known. Conventional LbL coating was carried out to obtain a multi-layered structure constituted from about 4 to 20 layers, and thus the production process may increase, to cause an increase in production costs.

PATENT LITERATURE

Patent Literature 1

Japanese Unexamined Patent Publication (Kokai) No. 54-81363

Patent Literature 2

Japanese Unexamined Patent Publication (Kokai) No. 54-24047

Patent Literature 3

Japanese Unexamined Patent Publication (Kokai) No. 56-51715

Patent Literature 4

Japanese Unexamined Patent Publication (Kokai) No. 59-229524

Patent Literature 5

Japanese Unexamined Patent Publication (Kokai) No. 2-188717

Patent Literature 6

Japanese Unexamined Patent Publication (Kokai) No. 5-5861

Patent Literature 7

Kohyo (National Publication of Translated Version) No. 2002-501211

Patent Literature 8

Kohyo (National Publication of Translated Version) No. 2005-538418

Patent Literature 9

Kohyo (National Publication of Translated Version) No. 2009-540369

SUMMARY OF THE INVENTION

The present invention provides a low water content soft lens for eye, wherein a phenomenon of adhesion of the lens to the cornea during wear, which has hitherto been regarded as a problem in a conventional low water content soft lens for eye, has been remarkably reduced or avoided. The present invention makes it possible to produce an excellent low water content soft lens for eye by a simple process at low costs.

The present invention includes the following constitutions according to exemplary embodiments.

The present invention provides a low water content soft lens for eye, including a base material, a layer made of an acidic polymer and a basic polymer being formed on at least a part of a surface of the base material.

In the above low water content soft lens for eye, the base material preferably contains, as a main component, a polymer of the following component A, or a copolymer of the following components A and B:

component A: a polysiloxane compound which has a plurality of polymerizable functional groups per molecule, and also has a number average molecular weight of 6,000 or more, and component B: a polymerizable monomer having a fluoroalkyl group.

The present invention also provides a method for producing a low water content soft lens for eye, which includes the following steps 1 to 3 in this order:

<Step 1>

Step of polymerizing a mixture of a component A which is polysiloxane compound having a plurality of polymerizable functional groups per molecule, and also having a number average molecular weight of 6,000 or more, and a component B which is a polymerizable monomer having a fluoroalkyl group, to obtain a lens-shaped molding;

<Step 2>

Step of bringing the molding obtained in the step 1 into contact with a basic polymer solution, and then washing the molding, to remove the surplus basic polymer solution; and <Step 3>

Step of bringing the molding obtained in the step 2 into contact with an acidic polymer solution, and then washing the molding, to remove the surplus acidic polymer solution.

According to the low water content soft lens for eye of the present invention, it is possible to remarkably reduce or avoid a phenomenon of adhesion of the lens to the cornea during wear, which has hitherto been regarded as a problem in a conventional low water content soft lens for eye. The low water content soft lens for eye of the present invention can reduce a risk of the growth of bacteria because of its low water content. According to a preferred aspect of the present invention, it is possible to provide a low water content soft lens for eye, which has high oxygen permeability and is excellent in water wettability, and which is flexible and is therefore excellent in comfort, and is also excellent in mechanical properties such as folding resistance. The low water content soft lens for eye of the present invention has a merit capable of producing by a simple process at low costs.

BRIEF DESCRIPTION OF THE DRAWINGS

FIG. 1 is a schematic view showing dynamic friction between a sample film and an artificial leather.

DETAILED DESCRIPTION OF THE INVENTION

In the low water content soft lens for eye of the present invention, "low water content" means that water content is 10% by weight or less. "Soft" means that tensile elastic modulus is 10 MPa or less.

The low water content soft lens for eye of the present invention can have features such as less feeling of dryness of eyes of wearers and excellent comfort because of its low water content. The low water content soft lens for eye of the present invention can have a merit such as low risk of the growth of bacteria because of its low water content. The water content is more preferably 5% or less, still more preferably 2% or less, and most preferably 1% or less. Too high water content is not preferred since feeling of dryness of eyes of ophthalmic lens wearers may increase or risk of the growth of bacteria may become higher.

Tensile elastic modulus of the low water content soft lens for eye of the present invention is preferably from 0.01 to 5 MPa, more preferably from 0.1 to 3 MPa, still more preferably from 0.1 to 2 MPa, even more preferably from 0.1 to 1 MPa, and most preferably from 0.1 to 0.6 MPa. When the tensile elastic modulus is too small, it may become difficult to handle since the lens is too soft. When the tensile elastic modulus is too large, comfort may become worse since the lens is too hard. It is preferred that the tensile elastic modulus becomes 2 MPa or less since satisfactory comfort is obtained, and that the tensile elastic modulus becomes 1 MPa or less since more satisfactory comfort is obtained. The tensile elastic modulus is measured by a specimen in a wet state.

Tensile elongation the low water content soft lens for eye of the present invention is preferably from 100% to 1,000%, and more preferably from 200% to 700%. It is not preferred that the tensile elongation is too small since the low water content soft lens for eye is likely to be broken. It is not preferred that the tensile elongation is too large since the low water content soft lens for eye is likely to be deformed. The tensile elongation is measured by a specimen in a wet state.

Dynamic contact angle (advancing angle, immersion rate of 0.1 mm/sec) of the lens for eye is preferably 100° or less, more preferably 90° or less, and still more preferably 80° or less. From the viewpoint of preventing adhesion to the cornea of the wearer, the dynamic contact angle is preferably lower, and is preferably 65° or less, more preferably 60° or less, still more preferably 55° or less, even more preferably 50° or less, and most preferably 45° or less.

From the viewpoint of preventing adhesion to the cornea of the wearer, liquid film retention time of a surface of a lens for eye is preferably long. As used herein, the liquid film retention time is the time during which a liquid film on a surface of a lens for eye is held without being broken, when the lens for eye immersed in a borate buffer is pulled up and then held in air so that a diameter direction becomes vertical. The liquid film retention time is preferably 5 seconds or more, more preferably 10 seconds or more, and most preferably 20 seconds or more.

From the viewpoint of preventing adhesion to the cornea of the wearer, the surface of the lens for eye preferably has excellent lubricity. As an indicator representing the lubricity, friction measured by the method mentioned in Examples of the present description is preferably smaller. The friction is preferably 60 gf or less, more preferably 50 gf or less, still more preferably 40 gf or less, and most preferably 30 gf or less. When the friction is extremely small, it may become difficult to handle when wearing and removing. Therefore, the friction is 5 gf or more, and preferably 10 gf or more.

Anti-fouling property of the lens for eye can be evaluated by adhesion of mucin, adhesion of lipid (methyl palmitate), and an artificial lacrimal fluid immersion test. The amount of adhesion determined by these evaluations is preferably as small as possible since the lens for eye is excellent in comfort, and also a risk of the growth of bacteria is reduced. The amount of adhesion of mucin is preferably 5 µg/cm$^2$ or less, more preferably 4 µg/cm$^2$ or less, and most preferably 3 µg/cm$^2$ or less.

From the viewpoint of supply of oxygen from atmospheric air to an eye of a wearer of the lens for eye, it is preferred or even required for a low water content soft lens for eye to have high oxygen permeability. The oxygen permeability [×10$^{11}$ (cm$^2$/sec) mLO$_2$/(mL·hPa)] is preferably from 50 to 2,000, more preferably from 100 to 1,500, still more preferably from 200 to 1,000, and most preferably from 300 to 700. It is not preferred that the oxygen permeability is excessively increased since an adverse influence may be sometimes exerted on other physical properties such as mechanical properties. The oxygen permeability is measured by a specimen in a dry state.

The low water content soft lens for eye of the present invention is a low water content soft lens for eye, preferably including a lens-shaped molding (hereinafter referred to as a base material) in which a layer made of acidic and basic polymers is formed on at least a part of a surface of the base material.

The base material preferably contains 5% by weight or more of silicon atoms in order to have high oxygen permeability, and to obtain strong adhesion with a polymer to be coated on a surface without involving in a covalent bond. The content (% by weight) of silicon atoms is calculated based on the weight of the base material in a dry state (100% by weight). The content of silicon atoms of the base material is preferably from 5% by weight to 36% by weight, more preferably from 7% by weight to 30% by weight, still more preferably from 10% by weight to 30% by weight, and most preferably from 12% by weight to 26% by weight. It is not preferred that the content of silicon atoms is too large since tensile elastic modulus may sometimes increase.

The content of silicon atoms in the base material can be measured by the following method. After weighing sufficiently dried base material in a platinum crucible, sulfuric acid is added then the base material is incinerated by heating using a hot plate and a burner. The obtained ash is melted with sodium carbonate and water is added. After dissolving by heating, nitric acid is added and the volume is fixed by water. Regarding this solution, silicon atoms are measured by ICP emission spectrometry and the content in the base material is determined.

The base material preferably contains, as a main component, a polymer of a component A: a polysiloxane compound which has a plurality of polymerizable functional groups per molecule, and also has a number average molecular weight of 6,000 or more, or a copolymer of the above component A and a compound which has a polymerizable functional group and is different from the component A. As used herein, the main component means a component which is contained in the amount of 50% by weight or more based on the weight of the base material in a dry state (100% by weight).

Number average molecular weight of the component A is preferably 6,000 or more. The present inventors have found that it is possible to obtain a low water content soft lens for eye, which is flexible and is excellent in comfort, and is also excellent in mechanical properties such as folding resistance, when the number average molecular weight of the component A is within the above range. The number average molecular weight of the polysiloxane compound as the component A is preferably 8,000 or more since it is possible to obtain a low water content soft lens for eye, which is more excellent in mechanical properties such as folding resistance. The number average molecular weight of the component A is preferably within a range from 8,000 to 100,000, more preferably from 9,000 to 70,000, and still more preferably from 10,000 to 50,000. When the number average molecular weight of the component A is too small, mechanical properties such as folding resistance may deteriorate. In particular, when the number average molecular weight is less than 6,000, folding resistance deteriorates. It is not preferred that the number average molecular weight of the component A is too large since flexibility and transparency may deteriorate.

It is preferred that the low water content soft lens for eye of the present invention has high transparency since it is an optical product. Regarding criteria of transparency, it is preferred that the soft lens is transparent with no turbidity when visually observed. Furthermore, when the lens for eye is observed by a lens projector, it is preferred that turbidity is scarcely or not observed, and it is most preferred that no turbidity is observed.

Dispersion degree (value obtained by dividing weight average molecular weight by number average molecular weight) of the component A is preferably 6 or less, more preferably 3 or less, still more preferably 2 or less, and most preferably 1.5 or less. When the dispersion degree of the component A is low, it is possible to achieve such benefits that compatibility with other components is improved and thus transparency of the obtained lens is improved; extractable components contained in the obtained lens reduce; and a ratio of shrinkage associated with lens molding decreases. The ratio of shrinkage associated with lens molding can be evaluated by a molding ratio of lens=[diameter of lens]/[diameter of cavity portion of mold]. As the molding ratio of lens approaches 1, it becomes easier to stably produce a high-quality lens. The molding ratio is preferably within a range from 0.85 to 2.0, more preferably from 0.9 to 1.5, and most preferably from 0.91 to 1.3.

In the present invention, number average molecular weight of the component A is polystyrene-equivalent number average molecular weight to be measured by a gel permeation chromatographic method (GPC method) using chloroform as a solvent. Weight average molecular weight and dispersion degree (value obtained by dividing weight average molecular weight by number average molecular weight) are also measured by a similar method.

In the present description, the weight average molecular weight is sometimes represented by Mw, and the number average molecular weight is sometimes represented by Mn. The molecular weight of 1,000 is sometimes written as 1 kD. For example, "Mw 33 kD" means "weight average molecular weight of 33,000".

The component A is a polysiloxane compound which has plurality of polymerizable functional groups. The number of polymerizable functional groups of the component A may be 2 or more per molecule, and preferably 2 per molecule from the viewpoint of easily obtaining more flexible (low elastic modulus) lens for eye. Particularly preferred is a structure having a polymerizable functional group at both ends of the molecular chain.

The polymerizable functional group of the component A is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, an citraconic acid residue and the like. Among these polymerizable functional groups, a (meth)acryloyl group is most preferable since it has high polymerizability.

In the present description, the term "(meth)acryloyl" represents both methacryloyl and acryloyl, and the same shall apply to terms such as (meth)acryl and (meth)acrylate.

The component A preferably has a structure of the following formula (A1).

[Chemical Formula 1]

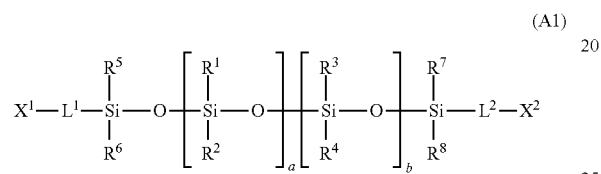

(A1)

In the formula (A1), $X^1$ and $X^2$ each independently represents a polymerizable functional group. $R^1$ to $R^6$ each independently represents a substituent selected from hydrogen, an alkyl group having 1 to 20 carbon atoms, a phenyl group and a fluoroalkyl group having 1 to 20 carbon atoms. $L^1$ and $L^2$ each independently represents a divalent group. a and b each independently represents the number of the respective repeating units.

$X^1$ and $X^2$ are preferably radical polymerizable functional groups, and radical polymerizable functional groups having a carbon-carbon double bond are preferable. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

Suitable specific examples of $R^1$ to $R^6$ include hydrogen; an alkyl group having 1 to 20 carbon atoms, such as a methyl group, an ethyl group, a propyl group, an isopropyl group, a butyl group, a t-butyl group, a decyl group, a dodecyl group or an octadecyl group; a phenyl group; and a fluoroalkyl group having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group or a nonadecafluorodecyl group. Among these groups, hydrogen and a methyl group are more preferable from the viewpoint of imparting satisfactory mechanical properties and high oxygen permeability to the lens for eye, and a methyl group is most preferable.

$L^1$ and $L^2$ are preferably divalent groups having 1 to 20 carbon atoms. Among these groups, groups represented by the following formulas (LE1) to (LE12) are preferable since a compound of the formula (A1) has an advantage of easily obtaining with high purity. Among these, $L^1$ and $L^2$ are more preferably groups represented by the following formulas (LE1), (LE3), (LE9) and (LE11), still more preferably groups represented by the following formulas (LE1) and (LE3), and most preferably a group represented by the following formula (LE1). In the following formulas (LE1) to (LE12), left side is drawn as an end which is bonded to a polymerizable functional group $X^1$ or $X^2$, while right side is drawn as an end which is bonded to a silicon atom.

[Chemical Formula 2]

| | |
|---|---|
| $OCH_2CH_2CH_2$ | (LE1) |
| $NHCH_2CH_2CH_2$ | (LE2) |
| $OCH_2CH_2NHCOOCH_2CH_2CH_2$ | (LE3) |
| $OCH_2CH_2NHCONHCH_2CH_2CH_2$ | (LE4) |
| $OCH_2CH_2CH_2CH_2$ | (LE5) |
| $NHCH_2CH_2CH_2CH_2$ | (LE6) |
| $OCH_2CH_2NHCOOCH_2CH_2CH_2CH_2$ | (LE7) |
| $OCH_2CH_2NHCONHCH_2CH_2CH_2CH_2$ | (LE8) |
| $OCH_2CH_2OCH_2CH_2CH_2$ | (LE9) |
| $NHCH_2CH_2OCH_2CH_2CH_2$ | (LE10) |
| $OCH_2CH_2NHCOOCH_2CH_2OCH_2CH_2CH_2$ | (LE11) |
| $OCH_2CH_2NHCONHCH_2CH_2OCH_2CH_2CH_2$ | (LE12) |

In the formula (A1), a and b each independently represents the number of the respective repeating units. Preferably, a and b each independently within a range from 0 to 1,500. The total value (a+b) of a and b is preferably 80 or more, more preferably 100 or more, still more preferably from 100 to 1400, even more preferably from 120 to 950, and yet more preferably from 130 to 700.

When all of $R^1$ to $R^6$ are methyl groups, b=0, and a is preferably from 80 to 1,500, more preferably from 100 to 1400, still more preferably from 120 to 950, and even more preferably from 130 to 700. In this case, the value of a is determined by the molecular weight of the polysiloxane compound as the component A.

The component A of the present invention may be used alone, or two or more kinds may be used in combination.

The other compound to be copolymerized with the component A is preferably a component B which is a polymerizable monomer having a fluoroalkyl group. The component B has properties of water and oil repellency due to a decrease in critical surface tension caused by a fluoroalkyl group, thereby exerting the effect of suppressing a surface of a lens for eye from being contaminated with components such as protein and lipid in a lacrimal fluid. The component B also has the effect of giving a low water content soft lens for eye, which is flexible and is excellent in comfort, and is also excellent in mechanical properties such as folding resistance. Suitable specific examples of the fluoroalkyl group of the component B include fluoroalkyl groups having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group and a nonadecafluorodecyl group. The fluoroalkyl group is more preferably a fluoroalkyl group having 2 to 8 carbon atoms, for example, a trifluoroethyl group, a tetrafluoropropyl group, a hexafluoroisopropyl group, an octafluoropentyl group or a dodecafluorooctyl group, and most preferably a trifluoroethyl group.

The polymerizable functional group of the component B is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

The component B is most preferably a (meth)acrylic acid fluoroalkyl ester since it exerts a remarkable effect of obtaining a low water content soft lens for eye, which is flexible and is excellent in comfort, and is also excellent in mechanical properties such as folding resistance. Specific examples of the (meth)acrylic acid fluoroalkyl ester include trifluoroethyl (meth)acrylate, tetrafluoroethyl (meth)acrylate, trifluoropropyl (meth)acrylate, tetrafluoropropyl (meth)acrylate, pentafluoropropyl (meth)acrylate, hexafluorobutyl (meth)acrylate, hexafluoroisopropyl (meth)acrylate, heptafluorobutyl (meth)acrylate, octafluoropentyl (meth)acrylate, nonafluoropentyl (meth)acrylate, dodecafluoropentyl (meth)acrylate, dodecafluoroheptyl (meth)acrylate, dodecafluorooctyl (meth)acrylate and tridecafluoroheptyl (meth)acrylate. Trifluoroethyl(meth)acrylate, tetrafluoroethyl (meth)acrylate, hexafluoroisopropyl (meth)acrylate, octafluoropentyl (meth) acrylate and dodecafluorooctyl (meth)acrylate, which are preferably used. Trifluoroethyl (meth)acrylate is most preferable.

The component B of the present invention may be used alone, or two or more kinds may be used in combination.

The content of the component B in the copolymer is preferably from 10 to 500 parts by weight, more preferably from 20 to 400 parts by weight, and still more preferably from 20 to 200 parts by weight, based on 100 parts by weight of the component A. When the use amount of the component B is too small, white turbidity may arise in the obtained lens for eye, or mechanical properties such as folding resistance may become insufficient.

It is possible to use, as the copolymer to be used in the base material, a copolymer obtained by copolymerizing a component which is different from the components A and B (hereinafter referred to as a component C), in addition to the components A and B.

The component C may be a component which decreases a glass transition point of a copolymer to room temperature or 0° C. or lower. The component decreases cohesive energy and therefore exerts the effect of imparting rubber elasticity and flexibility to the copolymer.

The polymerizable functional group of the component C is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

The component C, which is suitable for the improvement of mechanical properties such as flexibility and folding resistance, is a (meth)acrylic acid alkyl ester, and preferably a (meth)acrylic acid alkyl ester whose alkyl group has 1 to 20 carbon atoms, and specific examples thereof include methyl (meth)acrylate, ethyl (meth)acrylate, n-propyl (meth)acrylate, n-butyl (meth)acrylate, tert-butyl (meth)acrylate, isobutyl (meth)acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl (meth)acrylate, cyclopentyl (meth)acrylate, cyclohexyl (meth)acrylate, n-stearyl (meth)acrylate and the like. The (meth)acrylic acid alkyl ester is more preferably n-butyl(meth)acrylate, n-octyl (meth)acrylate, n-lauryl (meth)acrylate or n-stearyl (meth)acrylate. Among these, a (meth)acrylic acid alkyl ester whose alkyl group has 1 to 10 carbon atoms is more preferable. It is not preferred that the number of carbon atoms of the alkyl group is too large since transparency of the lens may sometimes deteriorate. Monofunctional (meth)acrylates having a siloxanyl group are also suitable for the improvement of oxygen permeability. As used herein, a siloxanyl group means a group having a Si—O—Si bond.

Furthermore, in order to improve mechanical properties, surface wettability, dimensional stability of the lens and the like, the below-mentioned monomer can be optionally copolymerized.

Examples of the monomer for the improvement of mechanical properties include an aromatic vinyl compound such as styrene, tert-butylstyrene and α-methylstyrene.

Examples of the monomer for the improvement of surface wettability include methacrylic acid, acrylic acid, itaconic acid, 2-hydroxyethyl methacrylate, 2-hydroxyethyl acrylate, 2-hydroxypropyl methacrylate, 2-hydroxypropyl acrylate, glycerol methacrylate, polyethylene glycol methacrylate, N,N-dimethylacrylamide, N-methyl acrylamide, dimethylaminoethyl methacrylate, methylenebisacrylamide, diacetone acrylamide, N-vinylpyrrolidone, N-vinylcaprolactam, N-vinyl acetamide, N-vinyl-N-methyl acetamide and the like. Among these monomers, an amide bond-containing monomer such as N,N-dimethylacrylamide, N-methyl acrylamide, dimethylaminoethyl methacrylate, methylenebisacrylamide, diacetoneacrylamide, N-vinylpyrrolidone, N-vinylcaprolactam, N-vinyl acetamide or N-vinyl-N-methyl acetamide is preferable.

Examples of the monomer for the improvement of dimensional stability of the lens include ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acryl methacrylate, and acrylates corresponding to these methacrylates, divinylbenzene, triallyl isocyanurate and the like.

The component C may be used alone, or two or more kinds may be used in combination.

The use amount of the component C is preferably from 0.001 to 400 parts by weight, more preferably from 0.01 to 300 parts by weight, still more preferably from 0.01 to 200 parts by weight, and most preferably from 0.01 to 30 parts by weight, based on 100 parts by weight of the component A. When the use amount of the component C is too small, it may become difficult to obtain the effect which is expected to the component C. When the use amount of the component C is too large, white turbidity may arise in the obtained lens for eye, or mechanical properties such as folding resistance may become insufficient.

The low water content soft lens for eye of the present invention may further contain a component such as an ultraviolet absorber, a pigment, a colorant, a humectant, a slip agent, a pharmaceutical and a nutritional supplementary component, a compatibilizing component, an antibacterial component, a mold release agent and the like. Any of the above-mentioned components can be contained in a non-reactive form or a copolymerization foam.

In the case of containing an ultraviolet absorber, it is possible to protect eyes of ophthalmic lens wearers from harmful ultraviolet rays. In the case of containing a colorant, the lens for eye is colored, results in easy identification and an improvement in convenience during handling.

Any of the above-mentioned components can be contained in the form of a non-reactive form or a copolymerization form. It is preferred that the above components are copolymerized, that is, an ultraviolet absorber having a polymerizable group or a colorant having a polymerizable group is used since the component is copolymerized with a base material and immobilized, and thus elution may scarcely occur.

The base material is preferably composed of components to be selected from an ultraviolet absorber and a colorant, and two or more kinds of components C other than these components (hereinafter referred to as a component Ck). In that case, it is preferred that at least one kind of the component Ck is selected from a (meth)acrylic acid alkyl ester having 1 to 10 carbon atoms, and at least one kind of the component Ck is selected from a monomer for the improvement of surface wettability. Use of two or more kinds of components Ck enhances affinity with an ultraviolet absorber or a colorant, and thus it becomes possible to obtain a transparent base material.

In the case of using an ultraviolet absorber, the use amount thereof is preferably from 0.01 to 20 parts by weight, more preferably from 0.05 to 10 parts by weight, and still more preferably from 0.1 to 2 parts by weight, based on 100 parts by weight of the component A. In the case of using a colorant, the use amount thereof is preferably from 0.00001 to 5 parts by weight, more preferably from 0.0001 to 1 part by weight, and still more preferably from 0.0001 to 0.5 part by weight, based on 100 parts by weight of the component A. When the content of the ultraviolet absorber or colorant is too small, it may become difficult to obtain the ultraviolet absorption effect or coloration effect. In contrast, when the content is too large, it may become difficult to dissolve these components in the base material. The use amount of the component Ck is preferably from 0.1 to 100 parts by weight, more preferably from 1 to 80 parts by weight, and still more preferably from 2 to 50 parts by weight, based on 100 parts by weight of the component A. When the use amount of the component Ck is too small, it may become difficult to obtain a transparent base material because of lack of affinity with the ultraviolet absorber or colorant. It is not preferred that the use amount of the component Ck is too large since white turbidity may arise in the obtained lens for eye, or mechanical properties such as folding resistance may become insufficient.

It is possible to use, as a method for producing a base material of a low water content soft lens for eye, that is, a lens-shaped molding, a known method. For example, it is possible to use a method in which a round bar- or plate-shaped polymer is once obtained and then processed into a desired shape by cutting or the like, a mold polymerization method, a spin-cast polymerization method and the like. In the case of obtaining a lens by cutting, freeze-cutting at low temperature is suitable.

A method of polymerizing a raw material composition containing a component A by a mold polymerization method to produce a lens for eye will be described below as an example. First, a gap between two mold members each having a fixed shape is filled with a raw material composition. Examples of the material of the mold member include resin, glass, ceramics, metal and the like. In the case of performing photopolymerization, since an optically transparent material is preferable, the resin or glass is preferably used. Depending on the shape of the mold member or properties of the raw material composition, a gasket may be used so as to impart a fixed thickness to the lens for eye, and to prevent liquid leakage of the raw material composition filled in the gap. The mold with the gap filled with raw material composition is subsequently irradiated with active rays such as ultraviolet rays, visible rays or a combination thereof, or heating in an oven or a liquid bath, thereby polymerizing the raw material composition filled in the mold. It is also possible to employ a method using two types of polymerization methods. That is, it is also possible to perform heat polymerization after photopolymerization, or perform photopolymerization after heat polymerization. In a specific aspect of photopolymerization, for example, light including ultraviolet rays such as light of a mercury lamp or an ultraviolet lamp (for example, FL15BL, Toshiba Corporation) are irradiated within a short time (usually 1 hour or less). In the case of performing heat polymerization, conditions of gradually raising a temperature of the composition from about room temperature and raising to the temperature of 60° C. to 200° C. over several hours to several tens of hours are preferably used so as to maintain optical uniformity and grade of a lens for eye, and to enhance reproducibility.

In the polymerization, a heat polymerization initiator typified by a peroxide or an azo compound, or a photopolymerization initiator is preferably added so as to facilitate the polymerization. In the case of performing heat polymerization, an initiator having optimum decomposition characteristics at a desired reaction temperature is selected. Commonly, an azo-based initiator and a peroxide-based initiator, each having a ten-hour half-life temperature of 40 to 120° C., are suitable. Examples of the photoinitiator in the case of performing photopolymerization include a carbonyl compound, a peroxide, an azo compound, a sulfur compound, a halogen compound, a metal salt and the like. These polymerization initiators are used alone or in combination. The amount of the polymerization initiator is preferably up to 5% by weight based on a polymerization mixture.

In the case of performing polymerization, a polymerization solvent can be used. Organic and inorganic various solvents can be applied as the solvent. Examples of the solvent include water; alcohol-based solvents such as methyl alcohol, ethyl alcohol, normal propyl alcohol, isopropyl alcohol, normal butyl alcohol, isobutyl alcohol, t-butyl alcohol, t-amyl alcohol, tetrahydrolinalool, ethylene glycol, diethylene glycol, triethylene glycol, tetraethylene glycol and polyethylene glycol; glycol ether-based solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether and polyethylene glycol dimethyl ether; ester-based solvents such as ethyl acetate, butyl acetate, amyl acetate, ethyl lactate and methyl benzoate; aliphatic hydrocarbon-based solvents such as normal hexane, normal heptane and normal octane; alicyclic hydrocarbon-based solvents such as cyclohexane and ethylcyclohexane; ketone-based solvents such as acetone, methyl ethyl ketone and methyl isobutyl ketone; aromatic hydrocarbon-based solvents such as benzene, toluene and xylene; and petroleum-based solvents. These solvent may be used alone, or two or more kinds may be used in combination.

It is advantageous that a layer made of an acidic polymer and a basic polymer (hereinafter referred to as a coating layer) is formed on at least a part of a surface of a base material in the low water content soft lens for eye of the present invention. Inclusion of a coating layer imparts satisfactory wettability and lubricity to the surface of the lens, and thus imparting excellent comfort.

The present inventors have found that, even if the low water content soft lens for eye of the present invention has low water content and is soft, and also the base material is neutral, it is possible to impart sufficient wettability, lubricity and anti-fouling property to the surface of the lens by forming a coating layer made of an acidic polymer and a basic polymer on the surface. Thereby, according to the low water content soft lens for eye of the present invention, it is possible to remarkably reduce or avoid a phenomenon of adhesion of the lens to the cornea during wear, which has hitherto been regarded as a problem in a conventional low water content soft lens for eye.

It is not necessary to have a covalent bond between the coating layer and the base material. It is preferred to have no covalent bond between the coating layer and the base material since it become possible to produce by a simple and easy step. The coating layer has practical durability even in the case of having no covalent bond between the coating layer and the base material.

The coating layer is preferably made of one or more kinds of acidic polymers and one or more kinds of basic polymers. Use of two or more kinds of acidic polymers or two or more kinds of basic polymers are more preferable since it is easy to develop properties such as lubricity and anti-fouling property to the surface of the lens for eye. In particular, use of two or more kinds of acidic polymers and one or more kinds of basic polymers are more preferable since this tendency is to be further increased.

The coating layer preferably includes one or more layers made of an acidic polymer (acidic polymer layer), and one or more layers made of a basic polymer (basic polymer layer).

The number of the acidic and basic polymer layers to be formed on the surface of the base material is preferably from 1 to 5, more preferably from 1 to 3, and still more preferably from 1 to 2. The number of the acidic polymer layer may be different from that of basic polymer layer.

The present inventors have found that excellent wettability and lubricity can be imparted by very small number of layers (total number of acidic and basic polymer layers is 2 or 3) in the low water content soft lens for eye of the present invention. This fact is crucially important for industry from the viewpoint of shortening of the production process. In that sense, in the low water content soft lens for eye of the present invention, the total number of acidic and basic polymer layers is preferably 2 or 3, and mot preferably 2.

The present inventors have also confirmed that wettability and lubricity are scarcely developed even if the coating layer only contains any one of acidic and basic polymers.

From the viewpoint of wettability, lubricity and shortening of the production process, the low water content soft lens for eye of the present invention preferably includes constitution selected from the following layer constitutions 1 to 4. In the following notations, molding means a lens-shaped molding, that is, a base material. The following notation shows layer constitution in which the respective layers are sequentially accumulated on a base material from left to right.

Layer constitution 1: Molding/basic polymer layer/acidic polymer layer

Layer constitution 2: Molding/acidic polymer layer/basic polymer layer

Layer constitution 3: Molding/basic polymer layer/acidic polymer layer/basic polymer layer Layer constitution 4: Molding/acidic polymer layer/basic polymer layer/acidic polymer layer Among these layer constitutions, layer constitution 1 and layer constitution 4 are more preferable since they exhibit particularly excellent wettability, and layer constitution 1 is most preferable from the viewpoint of production-related simplicity.

It is possible to suitably use, as the basic polymer, a homopolymer or copolymer having a plurality of groups having basicity along a polymer chain. An amino group and salts thereof are suitable as the group having basicity. Suitable examples of the basic polymer include an amino group-containing (meth)acrylate polymer such as poly(allylamine), poly(vinylamine), poly(ethyleneimine), poly(vinylbenzyltrimethylamine), polyaniline, poly(aminostyrene) or poly(N,N-dialkylaminoethyl methacrylate); an amino group-containing (meth)acrylamide polymer such as poly(N,N-dimethylaminopropyl acrylamide); and salts thereof. Although the followings are examples of a homopolymer, these copolymers (i.e., a copolymer of basic monomers composing the basic polymer, or a copolymer of a basic monomer and the other monomer) can also be suitably used.

When the basic polymer is a copolymer, the basic monomer composing the copolymer is preferably a monomer having an allyl group, a vinyl group and a (meth)acryloyl group from the viewpoint of high polymerizability, and most preferably a monomer having a (meth)acryloyl group. Suitable examples of the basic monomer composing the copolymer include allylamine, vinylamine (N-vinylcarboxylic acid amide as a precursor), vinylbenzyltrimethylamine, amino group-containing styrene, amino group-containing (meth)acrylate, amino group-containing (meth)acrylamide, and salts thereof. Among these monomers, amino group-containing (meth)acrylate, amino group-containing (meth)acrylamide, and salts thereof are more preferably from the viewpoint of high polymerizability, and N,N-dimethylaminoethyl methacrylate, N,N-dimethylaminopropyl acrylamide, and salts thereof are most preferable.

The basic polymer may be a polymer having a quaternary ammonium structure. The polymer having a quaternary ammonium structure compound can impart antimicrobial properties to a soft lens for eye when used for coating of the soft lens for eye.

It is possible to suitably use, as the acidic polymer, a homopolymer or copolymer having a plurality of groups having acidity along a polymer chain. The group having acidity is suitably a carboxyl group, a sulfonic acid group and salts thereof, and most suitably a carboxyl group and salts thereof. Examples of suitable acidic polymer include polymethacrylic acid, polyacrylic acid, poly(vinylbenzoic acid), poly(thiophene-3-acetic acid), poly(4-styrenesulfonic acid), polyvinylsulfonic acid, poly(2-acrylamide-2-methylpropanesulfonic acid) and salts thereof. Although the above polymers are examples of a homopolymer, these copolymers (i.e., a copolymer of basic monomers composing the basic polymer, or a copolymer of a basic monomer and the other monomer) can also be suitably used.

When the acidic polymer is a copolymer, the acidic monomer composing the copolymer is preferably a monomer having an allyl group, a vinyl group and a (meth)acryloyl group from the viewpoint of high polymerizability, and most preferably a monomer having a (meth)acryloyl group. Suitable examples of the acidic monomer composing the copolymer include (meth)acrylic acid, vinylbenzoic acid, styrenesulfonic acid, vinylsulfonic acid, 2-acrylamide-2-methylpropanesulfonic acid and salts thereof. Among these monomers, (meth)acrylic acid, 2-acrylamide-2-methylpropanesulfonic acid, and salts thereof are more preferable, and (meth)acrylic acid, and salts thereof are most preferable.

It is preferred that at least one kind of basic and acidic polymers is a polymer having a group selected from an amide bond and a hydroxyl group. It is preferred that a basic polymer and/or an acidic polymer has/have an amide bond since a surface having not only wettability but also lubricity can be formed. It is preferred that a basic polymer and/or an acidic polymer has/have a hydroxyl group since a surface having not only excellent wettability but also excellent anti-fouling property against a lacrimal fluid can be formed.

More preferably, two or more kinds of the acidic polymer and basic polymer are polymers having a group selected from a hydroxyl group and an amide bond. That is, the low water content soft lens for eye preferably contains two or more kinds selected from an acidic polymer having a hydroxyl group, a basic polymer having a hydroxyl group, an acidic polymer having an amide bond and a basic polymer having an amide bond. In this case, it is preferred since the effect of forming a surface having lubricity, or the effect capable of forming a surface having excellent anti-fouling property against a lacrimal fluid can be more remarkably exerted.

More preferably, the coating layer contains at least one kind selected from an acidic polymer having a hydroxyl group and a basic polymer having a hydroxyl group, and at least one kind selected from an acidic polymer having an amide bond and a basic polymer having an amide bond. In this case, it is preferred since both the effect of forming a surface having lubricity, and the effect capable of forming a surface having excellent anti-fouling property against a lacrimal fluid can be exerted.

Examples of the basic polymer having an amide bond include polyamides having an amino group, partially hydrolyzed chitosan, a copolymer of a basic monomer and a monomer having an amide bond and the like.

Examples of the acidic polymer having an amide bond include polyamides having a carboxyl group, a copolymer of an acidic monomer and a monomer having an amide bond and the like.

Examples of the basic polymer having a hydroxyl group include amino-polysaccharides such as chitin, a copolymer of a basic monomer and a monomer having a hydroxyl group and the like.

Examples of the acidic polymer having a hydroxyl group include polysaccharides having an acidic group such as hyaluronic acid, chondroitin sulfate, carboxymethyl cellulose and carboxypropyl cellulose, a copolymer of an acidic monomer and a monomer having an amide bond and the like.

The monomer having an amide bond is preferably a monomer having a (meth)acrylamide group and N-vinylcarboxylic acid amide (including a cyclic monomer) from the viewpoint of ease of polymerization. Suitable examples of the monomer include N-vinylpyrrolidone, N-vinylcaprolactam, N-vinyl acetamide, N-methyl-N-vinyl acetamide, N-vinylformamide, N,N-dimethylacrylamide, N,N-diethyl acrylamide, N-isopropyl acrylamide, N-(2-hydroxyethyl)acrylamide, acryloylmorpholine and acrylamide. Among these monomers, N-vinylpyrrolidone and N,N-dimethylacrylamide are preferable from the viewpoint of lubricity, and N,N-dimethylacrylamide is most preferable.

Suitable examples of the monomer having a hydroxyl group include hydroxyethyl(meth)acrylate, hydroxypropyl(meth)acrylate, hydroxybutyl (meth)acrylate, hydroxyethyl (meth)acrylamide, glycerol (meth)acrylate, caprolactone-modified 2-hydroxyethyl (meth)acrylate, N-(4-hydroxyphenyl)maleimide, hydroxystyrene and vinyl alcohol (carboxylic acid vinyl ester as a precursor). The monomer having a hydroxyl group is preferably a monomer having a (meth)acryloyl group from the viewpoint of ease of polymerization, and more preferably a (meth)acrylic acid ester monomer. Among these monomers, hydroxyethyl (meth)acrylate, hydroxypropyl (meth)acrylate and glycerol (meth)acrylate are preferable from the viewpoint of anti-fouling property against a lacrimal fluid, and hydroxyethyl (meth)acrylate is most preferable.

Specific examples of preferable copolymer of a basic monomer and a monomer having an amide bond include an N,N-dimethylaminoethyl methacrylate/N-vinylpyrrolidone copolymer, an N,N-dimethylaminoethyl methacrylate/N,N-dimethylacrylamide copolymer, an N,N-dimethylaminopropyl acrylamide/N-vinylpyrrolidone copolymer and an N,N-dimethylaminopropyl acrylamide/N,N-dimethylacrylamide copolymer. An N,N-dimethylaminopropyl acrylamide/N,N-dimethylacrylamide copolymer is most preferable.

Specific examples of preferable copolymer of an acidic monomer and a monomer having an amide bond include a (meth)acrylic acid/N-vinylpyrrolidone copolymer, a (meth)acrylic acid/N,N-dimethylacrylamide copolymer, a 2-acrylamide-2-methylpropanesulfonic acid/N-vinylpyrrolidone copolymer and a 2-acrylamide-2-methylpropanesulfonic acid/N,N-dimethylacrylamide copolymer. A (meth)acrylic acid/N,N-dimethylacrylamide copolymer is most preferable.

Specific examples of preferable copolymer of a basic monomer and a monomer having a hydroxyl group include an N,N-dimethylaminoethylmethacrylate/hydroxyethyl (meth)acrylate copolymer, an N,N-dimethylaminoethyl methacrylate/glycerol (meth)acrylate copolymer, an N,N-dimethylaminopropyl acrylamide/hydroxyethyl (meth)acrylate and an N,N-dimethylaminopropyl acrylamide/glycerol (meth)acrylate copolymer. An N,N-dimethylaminoethyl methacrylate/hydroxyethyl (meth)acrylate copolymer is most preferable.

Specific examples of preferable copolymer of an acidic monomer and a monomer having an amide bond include a (meth)acrylic acid/hydroxyethyl (meth)acrylate copolymer, a (meth)acrylic acid/glycerol (meth)acrylate copolymer, a 2-acrylamide-2-methylpropanesulfonic acid/hydroxyethyl (meth)acrylate copolymer and a 2-acrylamide-2-methylpropanesulfonic acid/glycerol (meth)acrylate copolymer. A (meth)acrylic acid/hydroxyethyl (meth)acrylate copolymer is most preferable.

In the case of using a copolymer of the basic monomer or acidic monomer and the other monomer, the copolymerization ratio [weight of basic monomer or acidic monomer]/[weight of the other monomer] is preferably from 1/99 to 99/1, more preferably from 2/98 to 90/10, and still more preferably from 10/90 to 80/20. When the copolymerization ratio is within the above range, functions such as lubricity and anti-fouling property against a lacrimal fluid are likely to be developed.

In order to change various characteristics, for example, thickness of the coating layer, it is possible to change molecular weights of an acidic polymer and a basic polymer. Specifically, when the molecular weight is increased, the thickness of the coating layer commonly increases. However, when the molecular weight is too large, it may become difficult to handle due to an increase in viscosity. Therefore, acidic and basic polymers to be used in the present invention preferably have a molecular weight of 2,000 to 150,000. The molecular weight is more preferably from 5,000 to 100,000, and still more preferably from 75,000 to 100,000. The molecular weight of the acidic and basic polymers is a polyethylene glycol-equivalent weight average molecular weight measured by a gel permeation chromatographic method (aqueous solvent).

Coating of the coating layer can be achieved by various methods disclosed, for example, in WO 99/35520, WO 01/57118 or U.S. Patent No. 2001-0045676.

An exemplary method for producing a low water content soft lens for eye of the present invention will be described below. The low water content soft lens for eye of the present invention can be obtained by respectively coating a surface of a lens-shaped molding (base material) with an acidic polymer solution and a basic polymer solution 1 to 5 times, more preferably 1 to 3 times, and still more preferably 1 to 2 times, to form a coating layer. The number of times of the coating step of an acidic polymer solution may be different from that of the coating step of a basic polymer solution.

The present inventors have found that excellent wettability and lubricity can be imparted by very small number of times of the coating steps (total number of coating steps of acidic and basic polymer solutions is 2 or 3) in the method for producing a low water content soft lens for eye of the present invention. This fact is crucially important for industry from the viewpoint of shortening of the production process. In that sense, the total number of coating steps of acidic and basic polymer solutions is preferably 2 or 3, and mot preferably 2.

The present inventors have also confirmed that wettability and lubricity are scarcely developed only by performing either the coating step of an acidic polymer solution or the coating step of a basic polymer solution once in the low water content soft lens for eye of the present invention.

From the viewpoint of wettability, lubricity and shortening of the production process, coating of the coating layer is preferably performed with the constitution selected from the following constitutions 1 to 4. The following notation shows that the respective coating steps are sequentially applied to a surface of a molding from left to right.

Constitution 1: Coating of basic polymer solution/coating of acidic polymer solution Constitution 2: Coating of acidic polymer solution/coating of basic polymer solution Constitution 3: Coating of basic polymer solution/coating of acidic polymer solution/coating of basic polymer solution Constitution 4: Coating of acidic polymer solution/coating of basic polymer solution/coating of acidic polymer solution Among these constitutions, constitution 1 and constitution 4 are more preferably since the obtained low water content soft lens for eye exhibits particularly excellent wettability, and constitution 1 is most preferably from the viewpoint of production-related simplicity.

In the case of coating an acidic polymer solution and a basic polymer solution, a surface of a base material may be untreated or already treated. As used herein, the phrase "surface of a base material is already treated" means that a surface of a base material is subjected to a surface treatment or surface modification by a known method. Suitable examples of the surface treatment or surface modification include a plasma treatment, a chemical modification, a chemical functionalization, a plasma coating and the like.

One of preferred aspects of the method for producing a low water content soft lens for eye of the present invention includes the following steps 1 to 3 in this order:
<Step 1>
Step of polymerizing a mixture of a component A which is polysiloxane compound having a plurality of polymerizable functional groups per molecule, and also having a number average molecular weight of 6,000 or more, and a component B which is a polymerizable monomer having a fluoroalkyl group, to obtain a lens-shaped molding;
<Step 2>
Step of bringing the molding obtained in the step 1 into contact with a basic polymer solution, and then washing the molding, to remove the surplus basic polymer solution; and
<Step 3>
Step of bringing the molding obtained in the step 2 into contact with an acidic polymer solution, and then washing the molding, to remove the surplus acidic polymer solution.

As mentioned above, a layer made of an acidic polymer and a basic polymer can be formed on a lens-shaped molding by sequentially bringing the molding into contact with an acidic polymer solution and a basic polymer solution. Thereafter, surplus polymer is preferably removed by sufficiently washing.

It is possible to apply, as the method of bringing the molding into contact with an acidic polymer solution or a basic polymer solution, various coating methods such as an immersion method (dipping method), a brush coating method, a spray coating method, a spin coating method, a die coating method and a squeegee method.

When contact with a solution is performed by an immersion method, immersion time can vary depending on various factors. Immersion of a molding in an acidic polymer solution or a basic polymer solution is preferably performed for 1 to 30 minutes, more preferably 2 to 20 minutes, and most preferably 1 to 5 minutes.

The concentration of acidic and basic polymer solutions can vary depending on properties of an acidic polymer or a basic polymer, thickness of a desired coating layer, and other various factors. The concentration of the acidic or basic polymer is preferably from 0.001 to 10% by weight, more preferably from 0.005 to 5% by weight, and most preferably from 0.01 to 3% by weight.

The pH of acidic and basic polymer solutions is preferably maintained within a range from 2 to 5, and more preferably from 2.5 to 4.5.

Removal of surplus acidic and basic polymers by washing is commonly performed by rinsing a molding after coating using clean water or an organic solvent. Rinsing is preferably performed by immersing the molding in water or an organic solvent or exposing to a water flow or an organic solvent flow. Rinsing may be completed in one step. However, it was recognized that it is efficient that a rinsing step is performed plural times. Rinsing is preferably performed in 2 to 5 steps. Immersion of each molding in a rinsing solution is preferably performed for 1 to 3 minutes.

Pure water is also preferably used as the rinsing solution. In order to increase adhesion of a coating layer, it is preferred to use an aqueous buffered solution having pH adjusted within a range from 2 to 7, more preferably from 2 to 5, and still more preferably from 2.5 to 4.5.

The step of drying or removing an excess rinsing solution may also be included. A molding can be dried to some extent by merely being left to stand under air atmosphere. Drying is preferably accelerated by supplying a mild air flow to the surface. Flow rate of the air flow can be adjusted as a function of the strength of a material to be dried, and mechanical fixturing of a material. It is not necessary to completely dry a molding. Herein, it is important to remove droplets of a solution adhered onto a surface of the molding as compared with drying of the molding. Therefore, the molding is only dried until a film of water or a solution on the surface of the mold is removed, resulting in shortening of the process time, favorably.

It is preferred that an acidic polymer and a basic polymer are alternately coated. It is possible to obtain a low water content soft lens for eye, which has excellent wettability and lubricity that cannot be obtained by a single layer, and also has excellent comfort that cannot be obtained by a single layer, by alternately coating the polymers.

The coating layer can be asymmetric. As used herein, "asymmetric" refers to the fact that a coating layer formed on a first side of a low water content soft lens for eye is different from that formed on a second side opposite the first side. As used herein, "different coating layer" refers to the fact that a coating layer formed on a first side and a coating layer formed on a second side each has different surface characteristics or functionalities.

The thickness of the coating layer can be controlled by adding one or more salts such as sodium chloride to an acidic or basic polymer solution. The concentration of the salt is preferably from 0.1 to 2.0% by weight. As the concentration of the salt increases, a polyelectrolyte exhibits a more spherical spatial structure. However, when the concentration becomes too high, even if the polyelectrolyte is deposited on a surface of a molding, it is not satisfactorily deposited. More preferably, the concentration of the salt is from 0.7 to 1.3% by weight.

The low water content soft lens for eye of the present invention is useful as a lens for eye, such as a low water content soft contact lens, an intraocular lens, an artificial cornea, a corneal inlay, a corneal onlay or a spectacle lens. The soft lens is particularly suitable as a low water content soft contact lens.

EXAMPLES

The present invention will be specifically described below by way of Examples, but the present invention is not limited thereto.

Analytical Method and Evaluation Method

In the present description, dry state means a state where a specimen is vacuum-dried at 40° C. for 16 hours, and then vacuum-dried at room temperature (25° C.) for 5 hours vacuum. The degree of vacuum in the vacuum drying is set to 2 hPa or less. The measurement of mechanical properties in a dry state is carried out as soon as possible after the vacuum drying.

In the present description, wet state means a state where a specimen is immersed in pure water at room temperature (25° C.) for 24 hours or more. The measurement of mechanical properties in a wet state is carried out as soon as possible after pulling out the specimen from pure water.

(1) Molecular Weight

Weight average molecular weight and number average molecular weight were measured by a GPC method under the following conditions.
Pump: TOSOH DP-8020
Detector: TOSOH RI-8010
Column oven: Shimadzu CTO-6A
Auto-sampler: TOSOH AS-8010
Column: TOSOH tskgel GMHHR-M (7.8 mm in inner diameter×30 cm, 5 μm in particle diameter)×two columns
Column temperature: 35° C.
Mobile phase: chloroform
Flow rate: 1.0 ml/minute
Sample concentration: 0.4% by weight
Injection amount: 100 μL
Standard sample: polystyrene (having a molecular weight of 1,010 to 1,090,000)

(2) Elongation

Using a prescribed blanking die, specimens each measuring 5 mm in width (minimum portion), 14 mm in length and about 0.2 mm in thickness were cut out from contact lens-shaped samples, and then stretched up to the length, which is 1.5 times (elongation of 50%) longer than an initial length, by hands. Five specimens were tested and the number of specimens, which were not broken, was written.

(3) Folding Resistance

A contact lens-shaped specimen was folded in two by fingers and then strongly rubbed by fingers. Five specimens were tested and judged by the following criteria.
A: All specimens are not failed.
B: Some specimens are not failed.
C: All specimens are failed with slight degree.
D: All specimens are failed with intermediate degree between C and E.
E: All specimens are failed to fragments.

(4) Transparency

A contact lens-shaped specimen was visually observed and transparency was evaluated by the following criteria.
A: Transparent with no turbidity
B: White turbidity to about intermediate degree between A and C
C: Semi-transparent with white turbidity.
D: White turbidity with about intermediate degree between C and E
E: White turbidity with no transparency (5) Water Content A contact lens-shaped specimen was used. The specimen was dried by a vacuum drying oven at 40° C. for 16 hours and weight (Wd) was measured. After the specimen was hydrated by immersing in pure water in a constant temperature bath at 40° C. at least overnight, water on a surface was wiped off by a wiping cloth ("Kimwipe®", manufactured by NIPPON PAPER CRECIA Co., LTD.) and weight (Ww) was measured. Water content was determined by the following equation. In the case the obtained value is less than 1%, it was judged as measurement limitation or less and was written as "less than 1%".

$$\text{Water content (\%)}=100\times(Ww-Wd)/Ww$$

(6) Water Wettability

A contact lens-shaped specimen was immersed in a borate buffer (pH 7.1 to 7.3) in a beaker at room temperature. The beaker containing the specimen and the borate buffer was exposed to ultrasonic using a ultrasonic cleaner (for 1 minute). The specimen was pulled up from the borate buffer and the specimen was held in air so that a diameter direction becomes vertical. A state of a surface of the specimen was visually observed, and then judged by the following criteria.
A: A liquid film on a surface is held for 20 seconds or more.
B: A liquid film on a surface is broken within 10 to 20 seconds.
C: A liquid film on a surface is broken within 5 to 10 seconds.
D: A liquid film on a surface is broken within 1 to 5 seconds.
E: A liquid film on a surface is broken instantly (within 1 second).

(7) Measurement of Dynamic Contact Angle

Using, as dynamic contact angle samples, film-shaped specimens each measuring 5 mm×10 mm×about 0.1 mm cut out from samples molded into a film, or strip-shaped specimens of 5 mm in width cut out from contact lens-shaped samples, advancing dynamic contact angle relative to a borate buffer (pH 7.1 to 7.3) was measured. An immersion rate was set to 0.1 mm/sec, and an immerse depth was set to 7 mm.

(8) Tensile Elastic Modulus, Elongation at Break

Using a prescribed blanking die, specimens each measuring 5 mm in width (minimum portion), 14 mm in length and 0.2 mm in thickness were cut out from contact lens-shaped samples. Using the specimens, a tensile test was carried out by a TENSILON Model RTM-100, manufactured by ORIENTEC Co., Ltd. A testing speed was 100 mm/minute, and a distance between grips (initial) was 5 mm.

(9) Lubricity

Lubricity was subjected to sensory evaluation after rubbing samples (contact lens shape) in a wet state five times with a finger of a person.

A: Excellent lubricity
B: About intermediate lubricity between A and C
C: Moderate lubricity
D: Little lubricity (about intermediate lubricity between C and E)
E: No lubricity

(10) Adhesion of Mucin

Mucin, Bovine Submaxillary Gland (Catalog No. 499643) manufactured by CALBIOCHEM Corporation was used as mucin. Contact lens-shaped samples were immersed in an aqueous mucin solution having a concentration of 0.1% under the conditions of 37° C. for 20 hours, and then the amount of mucin adhered to samples was determined by a bicinchoninic acid (BCA) protein assay method.

(11) Adhesion of Lipid

In a 500 ml beaker, a stirring bar (36 mm) was placed, and 1.5 g of methyl palmitate and 500 g of pure water were charged. A temperature of a water bath was set to 37° C. and the above beaker was placed in the center of the water bath, followed by stirring for one hour using a magnetic stirrer. A rotation speed was set to 600 rpm. Contact lens-shaped samples were put in a lens basket one by one and then put in the above beaker, followed by stirring. After 1 hour, stirring was stopped and samples in the lens basket were subjected to rubbing cleaning using city water at 40° C. and a liquid detergent for domestic use ("Mamalemon®", manufactured by Lion Corporation). After cleaning, samples were put in a screw tube containing a borate buffer (pH 7.1 to 7.3) and then immersed in an ice bath for 1 hour. After pulling out the screw tube from the ice bath, white turbidity of samples was visually observed and the amount of methyl palmitate adhered to samples was judged by the following criteria.

A: Transparent with no white turbidity
B: Slight white turbidity is observed
C: Considerable white turbidity is observed
D: White turbidity accounts for most part
E: White turbidity accounts for entirety

(12) Artificial Lacrimal Fluid Immersion Test

A tear-like fluid (TLF) buffer solution, which was prepared in accordance with the method disclosed in lines 5 to 36 on page 32 of WO 2008/127299 pamphlet, except that oleic acid is used in place of the oleic acid propyl ester, was used as an artificial lacrimal fluid. In 1 well of a multiplate for culture (24-well model, material: polystyrene, radiosterilized), 2 mL of an artificial lacrimal fluid was charged and then one sample (with contact lens shape) was immersed. Shaking was carried out at 100 rpm and 37° C. for 24 hours. After pulling out the sample, the sample was lightly washed with phosphate buffer solution (PBS) and then immersed in the well in which the artificial lacrimal fluid was replaced by 2 mL of an artificial lacrimal fluid. Furthermore, after shaking at 100 rpm and 37° C. for 24 hours, the sample was lightly washed with PBS and the amount of deposits was observed by visually evaluating the degree of white turbidity of the sample. The evaluation was carried out according to the following criteria.

A: No white turbidity is observed.
B: Slight white turbidity (less than 10% of area) is observed
C: Considerable white turbidity (10 to 50% of area) is observed
D: White turbidity accounts for most part (50 to 100% of area), while back side can be seen through
E: Thick white turbidity accounts for entirety, while back side cannot be easily seen through

(13) Transparency (Projector)

In a glass petri dish, a borate buffer (pH 7.1 to 7.3) was charged, and then a contact lens-shaped sample was placed. Using a universal projector (MODEL V-10A, manufactured by Nikon Corporation), transparency was visually observed when irradiating samples in a petri dish with light from above and below, and then evaluated according to the following criteria.

A: Transparent with no white turbidity
B: Slight white turbidity is observed
C: Considerable white turbidity is observed
D: White turbidity accounts for most part
E: White turbidity accounts for entirety

(14) Degree of Pigmentation

Degree of pigmentation (depth of blue color) of samples (contact lens shape) was visually observed and then evaluated according to the following criteria.

A: Coloration is recognized at a glance
B: About intermediate degree between A and C of pigmentation
C: Slight coloration is recognized
D: About intermediate degree between C and D of pigmentation
E: No coloration is recognized

(15) Lens Molding Ratio

Lens molding ratio was determined by dividing a diameters of a sample (with contact lens shape) by a diameter of a gap portion (having a shape corresponding to the sample shape) of a mold used for molding the sample.

(16) Friction

Using the apparatus shown in FIG. 1, a dynamic friction between a film, as a sample, and an artificial leather was measured. An artificial leather 1 ("SUPPLALE®", model number: PBZ13001, manufactured by Idemitsu Technofine Co., Ltd.) was stuck onto one surface of a glass plate measuring 26 mm×26 mm×1.4 mm to which a fishing line for pulling in a horizontal direction is attached. The artificial leather was stuck so that the back side faces outside. A film 2 measuring 60 mm×60 mm×0.25 mm in a wet state was placed on a horizontal rubber plate 3 and then a surface of the film was sufficiently wetted with a borate buffer (pH 7.1 to 7.3). The above glass plate was placed therein so that the artificial leather faces the film, and then a plastic container 4 containing small iron balls (the total weight of iron balls and a container is 50 g) was placed thereon. Using a tensile testing machine (RTM-100, manufactured by ORIENTEC Co., Ltd.), the fishing line attached to the glass plate was pulled at a rate of 100 mm/minute in a horizontal direction through a pulley. At this time, a dynamic friction between the artificial leather (back side) and the film was measured by a force to be applied to the tensile testing machine.

(17) Boiling Resistance

Samples (with contact lens shape) immersed in clean pure water were put in a closed vial bottle. Autoclave sterilization was carried out at 121° C. for 30 minutes, and then samples were cooled to room temperature. Five cycles were repeated, one cycle including a series of the above operations. Thereafter, the above-mentioned water wettability (6) was evaluated.

(18) Scrubbing Resistance a

Samples (with contact lens shape) were placed in the recess formed in the center of the flat of the hand and a cleaning solution ("OPTI FREE®", ALCON JAPAN LTD.) was added. After scrubbing front and back sides (each 10 times) by ball of the forefinger of another hand, samples were put in a screw tube containing clean "OPTI FREE®" and then left to stand for 4 hours or more. Fifteen cycles were repeated, provided that one cycle includes a series of the above operations. Samples were then washed with pure water and immersed in a borate buffer (pH 7.1 to 7.3). Thereafter, the above-mentioned water wettability (6) was evaluated.

(19) Scrubbing Resistance B

In the same manner as in (18), except for using "ReNU®" (Bausch & Lomb Incorporated) in place of "OPTI FREE", the evaluation was carried out.

Reference Example 1

Polydimethylsiloxane having a methacryloyl group at both ends (DMS-R31, Gelest, Inc., below-mentioned compound of the formula (M2), weight average molecular weight of 30,000, number average molecular weight of 13,000) (20 parts by weight) as a component A, trifluoroethyl acrylate (Biscoat 3F, Osaka Organic Chemical Industry Ltd.) (80 parts by weight) as a component B, IRGACURE® 1850 (Ciba Specialty Chemicals Inc., 2 parts by weight) and tetrahydrolinalool (20 parts by weight) were mixed and then stirred. As a result, a uniform and transparent monomer mixture was obtained. This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. In a glove box under a nitrogen atmosphere, the monomer mixture was injected into a mold for contact lens made of a transparent resin (poly-4-methylpentene-1) and then polymerized by irradiating with light (8,000 lux, 20 minutes) using a fluorescent lamp (Toshiba Corporation, FL-6D, quasi-daylight, 6W, 4 lamps). After polymerization, the whole mold was immersed in an aqueous 60% by weight isopropyl alcohol solution and a contact lens-shaped molding was removed from the mold. The obtained molding was immersed in a large excess amount of an aqueous 80% by weight isopropyl alcohol solution at 60° C. for 2 hours. Furthermore, the molding was immersed in a large excess amount of an aqueous 50% by weight isopropyl alcohol solution at room temperature for 30 minutes, followed by immersion in a large excess amount of an aqueous 25% by weight isopropyl alcohol solution at room temperature for 30 minutes, and further immersion in a large excess amount of pure water at room temperature for 30 minutes. Finally, the molding immersed in clean pure water was put in a closed vial bottle, and then autoclave sterilization was carried out at 121° C. for 30 minutes. The obtained molding had a water content of less than 1%. The evaluation results of the obtained molding are shown in Table 1.

Reference Examples 2 to 12

In the very same manner as in Reference Example 1, except that the use amounts of components A and B were changed to amounts shown in Table 1, moldings were obtained. Both the obtained moldings had a water content of less than 1%. The evaluation results of the obtained molding are shown in Table 1.

TABLE 1

| | Component A DMS-R31 (Parts by weight) | Component B Biscoat 3F (Parts by weight) | Si atom Content (% by weight) | Evaluation results | | | | |
|---|---|---|---|---|---|---|---|---|
| | | | | Transparency | Elongation (number of specimens which were not broken) | Folding resistance | Tensile elastic modulus (kPa) | Elongation at break (%) |
| Reference Example 1 | 20 | 80 | 7.4 | | | | | |
| Reference Example 2 | 40 | 60 | 15 | A | 5 | A | 450 | 400 |
| Reference Example 3 | 45 | 55 | 17 | A | 5 | A | 510 | 250 |
| Reference Example 4 | 50 | 50 | 19 | A | 5 | A | Unevaluated | Unevaluated |
| Reference Example 5 | 55 | 45 | 20 | B | 5 | A | Unevaluated | Unevaluated |
| Reference Example 6 | 60 | 40 | 22 | C | 5 | A | 560 | 270 |
| Reference Example 7 | 65 | 35 | 24 | C | 5 | A | Unevaluated | Unevaluated |
| Reference Example 8 | 70 | 30 | 26 | C | 5 | A | Unevaluated | Unevaluated |
| Reference Example 9 | 75 | 25 | 28 | C | 5 | A | Unevaluated | Unevaluated |
| Reference Example 10 | 80 | 20 | 30 | C | 5 | A | 470 | 270 |
| Reference Example 11 | 100 | 0 | 37 | D | 3 | A | Unevaluated | Unevaluated |
| Reference Example 12 | 0 | 100 | — | *1 | *1 | *1 | *1 | *1 |

*1: failed to mold into a lens shape due to poor polymerization

Reference Examples 13 to 19

In the very same manner as in Reference Example 1, except that polydimethylsiloxane having a methacryloyl group at both ends (DMS-R22, Gelest, Inc., below-mentioned compound of the formula (M2), weight average molecular weight of 8,300, number average molecular weight of 7,400) was used in the amount shown in Table 2 as a component A, and that trifluoroethyl acrylate (Biscoat 3F, Osaka Organic Chemical Industry Ltd.) was used in the amount shown in Table 2 as a component B, moldings were obtained. The obtained molding had a water content of less than 1%. The evaluation results of the obtained molding are shown in Table 2.

TABLE 2

|  | Component A DMS-R22 (Parts by weight) | Component B Biscoat 3F (Parts by weight) | Si atom content (% by weight) | Transparency | Elongation (number of specimens which were not broken) | Folding resistance | Tensile elastic modulus (kPa) | Elongation at break (%) |
|---|---|---|---|---|---|---|---|---|
| Reference Example 13 | 10 | 90 | 3.7 | C | 5 | B | Unevaluated | Unevaluated |
| Reference Example 14 | 20 | 80 | 7.3 | A | 5 | B | 630 | 190 |
| Reference Example 15 | 40 | 60 | 15 | A | 5 | B | 960 | 170 |
| Reference Example 16 | 50 | 50 | 18 | A | 5 | C | Unevaluated | Unevaluated |
| Reference Example 17 | 60 | 40 | 22 | A | 4 | E | 1140 | 90 |
| Reference Example 18 | 80 | 20 | 29 | A | 4 | E | 1110 | 80 |
| Reference Example 19 | 100 | 0 | 37 | A | 4 | E | 920 | 160 |

Reference Examples 20 to 24

In the very same manner as in Reference Example 1, except that polydimethylsiloxane having a methacryloyl group at both ends (X-22-164C, Shin-Etsu Chemical Co., Ltd., weight average molecular weight of 7,200, number average molecular weight of 4,800) (50 parts by weight) was used as a component A, and that the monomer having a fluoroalkyl group (50 parts by weight) shown in Table 3 was used as a component B, moldings were obtained. The evaluation results of the obtained molding are shown in Table 3.

TABLE 3

|  | Component A X-22-164C (Parts by weight) | Component B Name | Component B (Parts by weight) | Si atom content (% by weight) | Transparency | Elongation (number of specimens which were not broken) | Folding resistance |
|---|---|---|---|---|---|---|---|
| Reference Example 20 | 50 | Biscoat 3FM | 50 | 18 | A | 2 | D |
| Reference Example 21 | 50 | Biscoat 8F | 50 | 18 | B | 0 | E |
| Reference Example 22 | 50 | Biscoat 3F | 50 | 18 | A | 1 | D |
| Reference Example 23 | 50 | Biscoat 17F | 50 | — | *1 | *1 | *1 |
| Reference Example 24 | 50 | HFIP-M | 50 | 18 | A | 0 | D |

*1: abandoned polymerization because of phase separation of polymerization raw solution
Biscoat 3FM: Trifluoroethylmethacrylate (Osaka Organic Chemical Industry Ltd.)
Biscoat 8F: Octafluoropentyl acrylate (Osaka Organic Chemical Industry Ltd.)
Biscoat 3F: Trifluoroethyl acrylate (Osaka Organic Chemical Industry Ltd.)
Biscoat 17F: Heptadecafluorodecyl acrylate (Osaka Organic Chemical Industry Ltd.)
HFIP-M: Hexafluoroisopropyl methacrylate (Central Glass Co., Ltd.).

Reference Examples 25 to 37

In the very same manner as in Reference Example 1, except that the polydimethylsiloxane having a methacryloyl group at both ends shown in Table 4 (below-mentioned compound of the formula (M2)) was used in the amount shown in Table 4 as a component A, the component B was not used, and the monomer shown in Table (50 parts by weight) was used in the amount shown in Table 4 as a component C, moldings were obtained. The evaluation results of the obtained molding are shown in Table 4.

TABLE 4

|  | Component A Name | Component A Weight average molecular weight | Component A Number average molecular weight | Component A Parts by weight | Component C Name | Component C Parts by weight | Si atom content (% by weight) | Transparency | Elongation (number of specimens which were not broken) | Folding resistance |
|---|---|---|---|---|---|---|---|---|---|---|
| Reference Example 25 | X-22-164A | 3,100 | 2,300 | 50 | Butyl acrylate | 50 | 17 | A | 0 | E |
| Reference Example 26 | X-22-164B | 5,200 | 3,700 | 50 | Butyl acrylate | 50 | 18 | A | 0 | D |

TABLE 4-continued

| | Component A | | | Component C | | Si atom | | Evaluation results | |
|---|---|---|---|---|---|---|---|---|---|
| | Name | Weight average molecular weight | Number average molecular weight | Parts by weight | Name | Parts by weight | content (% by weight) | Transparency | Elongation (number of specimens which were not broken) | Folding resistance |
| Reference Example 27 | X-22-164C | 7,200 | 4,800 | 50 | Butyl acrylate | 50 | 18 | B | 1 | D |
| Reference Example 28 | X-22-164C | 7,200 | 4,800 | 50 | N,N-dimethyl acrylamide | 50 | 18 | E | 0 | E |
| Reference Example 29 | X-22-164A | 3,100 | 2,300 | 50 | 2-ethylhexyl acrylate | 50 | 17 | D | 0 | D |
| Reference Example 30 | X-22-164B | 5,200 | 3,700 | 50 | 2-ethylhexyl acrylate | 50 | 18 | D | 0 | D |
| Reference Example 31 | X-22-164C | 7,200 | 4,800 | 50 | 2-ethylhexyl acrylate | 50 | 18 | B | 1 | D |
| Reference Example 32 | DMS-R31 | 30,000 | 13,000 | 50 | Butyl acrylate | 50 | 19 | B | 5 | A |
| Reference Example 33 | DMS-R22 | 8,300 | 7,400 | 50 | Butyl acrylate | 50 | 18 | B | 5 | A |
| Reference Example 34 | DMS-R31 | 30,000 | 13,000 | 50 | 2-ethylhexyl acrylate | 50 | 19 | A | 5 | A |
| Reference Example 35 | DMS-R22 | 8,300 | 7,400 | 50 | 2-ethylhexyl acrylate | 50 | 18 | A | 5 | A |
| Reference Example 36 | Synthesized compound 1 | 113,000 | 75,000 | 50 | 2-ethylhexyl acrylate | 50 | 19 | B | 5 | A |
| Reference Example 37 | Synthesized compound 2 | 157,000 | 103,000 | 50 | 2-ethylhexyl acrylate | 50 | 19 | D | 4 | B |

Synthesized compound 1: synthesized in laboratory by inventors
Synthesized compound 2: synthesized in laboratory by inventors

SYNTHESIS EXAMPLES

Synthesis Examples of copolymers used for coating in Examples are shown. In Synthesis Examples, molecular weight of each copolymer was measured under the following conditions.
(GPC Measurement Conditions)
Apparatus: Prominence GPC system, manufactured by Shimadzu Corporation
Pump: LC-20AD
Auto-sampler: SIL-20AHT
Column oven: CTO-20A
Detector: RID-10A
Column: manufactured by TOSOH CORPORATION GMP-WXL (7.8 mm in inner diameter×30 cm, 13 μm in particle diameter)
Solvent: water/methanol=1/1 (addition of 0.1N lithium nitrate)
Flow rate: 0.5 ml/minute
Measurement time: 30 minutes
Sample concentration: 0.1% by weight
Injection amount: 100 μL
Standard sample: Polyethylene oxide standard sample, manufactured by Agilent (0.1 kD to 1,258 kD).

Synthesis Example 1

CPVPA: N-Vinylpyrrolidone/Acrylic Acid (Molar Ratio of 2/1)

In a 500 mL three-necked flask, N-vinylpyrrolidone (66.68 g, 0.60 mol), acrylic acid (21.62 g, 0.30 mol), dimethyl sulfoxide (353.96 g), a polymerization initiator VA-061 (Wako Pure Chemical Industries, Ltd., 0.1408 g, 0.562 mmol) and 2-mercaptoethanol (43.8 μL, 0.63 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 50° C. for 0.5 hours, followed by temperature rise to 70° C. and further stirring for 6.5 hours. After completion of the polymerization, the polymerization reaction solution was cooled to room temperature and 100 mL of water was added, and then the solution was poured into 400 mL of acetone and the mixed solution was left to stand overnight. On the next day, 200 mL of acetone was further added and the solution was left to stand, and then the supernatant was removed by decantation. The obtained solid component was washed seven times with acetone/water (=400 mL/100 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 46 kD, Mw: 180 kD (Mw/Mn=3.9).

Synthesis Example 2

CPVPA: N-Vinylpyrrolidone/Acrylic Acid (Molar Ratio of 1/2)

In a 500 mL three-necked flask, N-vinylpyrrolidone (33.34 g, 0.30 mol), acrylic acid (43.24 g, 0.60 mol), dimethyl sulfoxide (307.08 g), a polymerization initiator VA-061 (Wako Pure Chemical Industries, Ltd., 0.1408 g, 0.562 mmol) and 2-mercaptoethanol (43.8 μL, 0.63 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 50° C. for 0.5 hours, followed by temperature rise to 70° C. and further stirring for 6.5 hours. After completion of the polymerization, the polymerization reaction solution was cooled to room temperature and 100 mL of water was added, and then the solution was poured into 500 mL of acetone and the mixed solution was left to stand overnight. On the next day, 200 mL of acetone was further added and then the supernatant was removed by decantation. The obtained solid component was washed seven times with acetone/water (=700 mL/100 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 65 kD, Mw: 202 kD (Mw/Mn=3.1).

Synthesis Example 3

CPVPA: N-Vinylpyrrolidone/Acrylic Acid (Molar Ratio of 90/10)

In a 500 mL three-necked flask, N-vinylpyrrolidone (NVP, 90.02 g, 0.81 mol), acrylic acid (6.49 g, 0.09 mol), dimethyl sulfoxide (386.8 g), a polymerization initiator VA-061 (Wako Pure Chemical Industries, Ltd., 0.1408 g, 0.562 mmol) and 2-mercaptoethanol (2-ME, 43.8 μL, 0.63 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 50° C. for 0.5 hours, followed by temperature rise to 70° C. and further stirring for 6.5 hours. After completion of the polymerization, the polymerization reaction solution was cooled to room temperature and 100 mL of water was added, and then the solution was poured into 500 mL of acetone and the mixed solution was left to stand overnight. On the next day, 200 mL of acetone was further added and 100 mL of hexane was added, and then the supernatant was removed by decantation. The obtained solid component was washed seven times with acetone/water (=500 mL/100 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 35 kD, Mw: 130 kD (Mw/Mn=3.8).

Synthesis Example 4

CPVPA: N-Vinylpyrrolidone/Acrylic Acid (Molar Ratio of 80/20)

In the same manner as in Synthesis Example 3, except that 0.72 mol of N-vinylpyrrolidone and 0.18 mol of acrylic acid were respectively used, a copolymer was obtained. The thus obtained copolymer had a molecular weight of Mn: 45 kD, Mw: 193 kD (Mw/Mn=4.4).

Synthesis Example 5

CPDA: N,N-Dimethylacrylamide/Acrylic Acid (Molar Ratio of 2/1)

In a 500 mL three-necked flask, N,N-dimethylacrylamide (59.50 g, 0.600 mol), acrylic acid (21.62 g, 0.300 mol), pure water (325.20 g), a polymerization initiator VA-061 (Wako Pure Chemical Industries, Ltd., 0.1408 g, 0.562 mmol) and 2-mercaptoethanol (43.8 μL, 0.63 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 50° C. for 0.5 hours, followed by temperature rise to 70° C. and further stirring for 6.5 hours. After completion of the polymerization, the polymerization reaction solution was concentrated up to 400 g by an evaporator, and then the solution was poured into 2-propanol/n-hexane (=500 mL/500 mL). After being left to stand, the supernatant was removed by decantation. The obtained solid component was washed three times with 2-propanol/n-hexane (=250 mL/250 mL). The solid component was washed seven times with acetone/water (=500 mL/100 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 55 kD, Mw: 192 kD (Mw/Mn=3.5).

Synthesis Example 6

CPDA: N,N-Dimethylacrylamide/Acrylic Acid (Molar Ratio of 1/2)

In a 500 mL three-necked flask, N,N-dimethylacrylamide (29.70 g, 0.300 mol), acrylic acid (43.20 g, 0.600 mol), pure water (292.40 g), a polymerization initiator VA-061 (Wako Pure Chemical Industries, Ltd., 0.1408 g, 0.562 mmol) and 2-mercaptoethanol (43.8 μL, 0.63 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 50° C. for 0.5 hours, followed by temperature rise to 70° C. and further stirring for 6.5 hours. After completion of the polymerization, the polymerization reaction solution was concentrated up to 350 g by an evaporator, and then the solution was poured into 2-propanol/n-hexane (=500 mL/500 mL). After being left to stand, the supernatant was removed by decantation. The obtained solid component was washed three times with 2-propanol/n-hexane (=250 mL/250 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 87 kD, Mw: 235 kD (Mw/Mn=2.7).

Synthesis Example 7

CPDA: N,N-Dimethylacrylamide/Acrylic Acid (Molar Ratio of 90/10)

In a 500 mL three-necked flask, N,N-dimethylacrylamide (DMA, 80.30 g, 0.810 mol), acrylic acid (6.49 g, 0.090 mol), pure water (347.90 g), a polymerization initiator VA-061 (Wako Pure Chemical Industries, Ltd., 0.1408 g, 0.562 mmol) and 2-mercaptoethanol (2-ME, 43.8 μL, 0.63 mmol) were charged, and then equipped with a three-way stop-cock, a reflux condenser tube, a thermometer and a mechanical stirrer. The concentration of the monomer was 20% by weight.

After degassing inside the three-necked flask using a vacuum pump and repeating replacement by argon three times, stirring was carried out at 50° C. for 0.5 hours, followed by temperature rise to 70° C. and further stirring for 6.5 hours. After completion of the polymerization, the polymerization reaction solution was concentrated up to 470 g by an evaporator, and then the solution was poured into 2-propanol/n-hexane (=500 mL/500 mL). After being left to stand, the supernatant was removed by decantation. The obtained solid component was washed five times with 2-propanol/n-hexane (=250 mL/250 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 54 kD, Mw: 162 kD (Mw/Mn=3.0).

Synthesis Example 8

CPDA: N,N-Dimethylacrylamide/Acrylic Acid
(Molar Ratio of 95/5)

In a three-necked flask, N,N-dimethylacrylamide (DMA, 0.19 mol), acrylic acid (AA, 0.01 mol), pure water, a polymerization initiator VA-061 (Wako Pure Chemical Industries, Ltd., 0.093 mmol) and 2-mercaptoethanol (2-ME, 0.07 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 50° C. for 0.5 hours, followed by temperature rise to 70° C. and further stirring for 6.5 hours. After completion of the polymerization, the polymerization reaction solution was concentrated up to 350 g by an evaporator, and then the solution was poured into 2-propanol/n-hexane (=200 mL/200 mL). After being left to stand, the supernatant was removed by decantation. The obtained solid component was washed three times with 2-propanol/n-hexane (=100 mL/100 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 77 kD, Mw: 229 kD.

Synthesis Examples 9 to 16

CPDA: N,N-Dimethylacrylamide/Acrylic Acid

Polymers were obtained by the same procedure as in Synthesis Example 8, except that amounts and concentrations of monomers of N,N-dimethylacrylamide (DMA), acrylic acid (AA), a polymerization initiator VA-061 and 2-mercaptoethanol (2-ME) were set to values shown in Table 5.

TABLE 5

|  | DMA (mol) | AA (mol) | VA-061 (mmol) | 2-ME (mmol) | Monomer concentration (% by weight) |
| --- | --- | --- | --- | --- | --- |
| Synthesis Example 8 | 0.19 | 0.01 | 0.093 | 0.070 | 20 |
| Synthesis Example 9 | 0.16 | 0.04 | 0.124 | 0.140 | 20 |
| Synthesis Example 10 | 0.10 | 0.10 | 0.124 | 0.140 | 20 |
| Synthesis Example 11 | 0.19 | 0.01 | 0.031 | 0.035 | 15 |
| Synthesis Example 12 | 0.16 | 0.04 | 0.031 | 0.035 | 15 |
| Synthesis Example 13 | 0.10 | 0.10 | 0.031 | 0.035 | 15 |

TABLE 5-continued

|  | DMA (mol) | AA (mol) | VA-061 (mmol) | 2-ME (mmol) | Monomer concentration (% by weight) |
| --- | --- | --- | --- | --- | --- |
| Synthesis Example 14 | 0.19 | 0.01 | 0.015 | 0.017 | 15 |
| Synthesis Example 15 | 0.16 | 0.04 | 0.025 | 0.023 | 15 |
| Synthesis Example 16 | 0.10 | 0.10 | 0.025 | 0.035 | 15 |

Synthesis Example 17

CPDEAC: N,N-Diethyl
Acrylamide/Acryloylmorpholine

In a 300 mL three-necked flask, N,N-diethyl acrylamide (12.71 g, 0.100 mol), N-acryloylmorpholine (14.12 g, 0.100 mol), t-amyl alcohol (63.20 g), a polymerization initiator VA-061 (Wako Pure Chemical Industries, Ltd., 0.0310 g, 0.124 mmol) were charged, and then equipped with a three-way stop-cock, a reflux condenser tube, a thermometer and a mechanical stirrer. The concentration of the monomer was 30% by weight. After degassing inside the three-necked flask using a vacuum pump and repeating replacement by argon three times, stirring was carried out at 70° C. for 1 hour, followed by temperature rise to 75° C. and further stirring for 4 hours. After completion of the polymerization, the polymerization reaction solution was cooled to room temperature and the solvent was distilled off by an evaporator, and then washed once with each of n-hexane/methanol (=300 mL/80 mL, 130 mL/35 mL, 100 mL/20 mL and 100 mL/10 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 49 kD, Mw: 162 kD (Mw/Mn=3.3).

Synthesis Example 18

CPACDM:
Acryloylmorpholine/N,N-Dimethylacrylamide

In a 300 mL three-necked flask, N-acryloylmorpholine (14.20 g, 0.101 mol), N,N-dimethylacrylamide (DMA, 9.92 g, 0.100 mol), t-amyl alcohol (96.63 g), a polymerization initiator VA-061 (Wako Pure Chemical Industries, Ltd., 0.0310 g, 0.124 mmol), 2-mercaptoethanol (86 μL, 1.23 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 70° C. for 1 hour, followed by temperature rise to 75° C. and further stirring for 4 hours. After completion of the polymerization, the polymerization reaction solution was cooled to room temperature and the solvent was distilled off by an evaporator, and then washed once with each of n-hexane/methanol (=400 mL/30 mL, 500 mL/40 mL, 130 mL/3 mL and 200 mL/7 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 4.3 kD, Mw: 17 kD (Mw/Mn=4.1)).

Synthesis Example 19

CPDEDM: N,N-Diethyl Acrylamide/N,N-Dimethylacrylamide

In a 300 mL three-necked flask, N,N-diethyl acrylamide (DEAA, 19.22 g, 0.151 mol), N,N-dimethylacrylamide (DMA, 14.88 g, 0.150 mol), TAA (104.65 g) and a polymerization initiator VA-061 (Wako Pure Chemical Industries, Ltd., 0.0465 g, 0.186 mmol) were charged, and then equipped with a three-way stop-cock, a reflux condenser tube, a thermometer and a mechanical stirrer. The concentration of the monomer was 25% by weight. After degassing inside the three-necked flask using a vacuum pump and repeating replacement by argon three times, stirring was carried out at 70° C. for 1.5 hours, followed by temperature rise to 75° C. and further stirring for 3.5 hours. After completion of the polymerization, the polymerization reaction solution was cooled to room temperature and the solvent was distilled off by an evaporator, and then washed once with each of n-hexane/methanol (=500 mL/0 mL, 250 mL/25 mL, 200 mL/30 mL and 200 mL/3 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 90 kD, Mw: 327 kD (Mw/Mn=3.7).

Synthesis Example 20

CPHEDM: N-(2-Hydroxyethyl)Acrylamide/N,N-Dimethylacrylamide

In a 300 mL three-necked flask, N-(2-hydroxyethyl)acrylamide (15.04 g, 0.100 mol), N,N-dimethylacrylamide (9.96 g, 0.100 mol), t-amyl alcohol (99.80 g), polymerization initiator VA-061 (Wako Pure Chemical Industries, Ltd., 0.0310 g, 0.124 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 70° C. for 1 hour, followed by temperature rise to 75° C. and further stirring for 4 hours. After completion of the polymerization, the polymerization reaction solution was cooled to room temperature and the solvent was distilled off by an evaporator, and then washed once with each of n-hexane/methanol (=200 mL/100 mL, 200 mL/100 mL, 100 mL/40 mL and 100 mL/60 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 109 kD, Mw: 660 kD (Mw/Mn=6.1).

Synthesis Example 21

CPHA: 2-Hydroxyethyl Methacrylate/Acrylic Acid (Molar Ratio of 3/1)

In a 300 mL three-necked flask, 2-hydroxyethyl methacrylate (HEMA, 17.1 g, 0.15 mol), acrylic acid (AA, 3.6 g, 0.05 mol), dimethyl sulfoxide (48.4 g) and a polymerization initiator VA-061 (Wako Pure Chemical Industries, Ltd., 0.0310 g, 0.124 mmol) were charged, and then equipped with a three-way stop-cock, a reflux condenser tube, a thermometer and a mechanical stirrer. The concentration of the monomer was 30% by weight. After degassing inside the three-necked flask using a vacuum pump and repeating replacement by argon three times, stirring was carried out at 60° C. for 0.5 hours, followed by temperature rise to 70° C. and further stirring for 4.5 hours. After completion of the polymerization, the polymerization reaction solution was cooled to room temperature and 100 mL of ethanol was added, and then the mixed solution was poured into 500 mL of water and left to stand overnight. On the next day, the supernatant was discarded and the obtained solid component was further washed twice with 500 mL of water. The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 61 kD, Mw: 267 kD (Mw/Mn=4.4).

Synthesis Example 22

CPHA: 2-Hydroxyethyl Methacrylate/Acrylic Acid (Molar Ratio of 3/1)

In a 300 mL three-necked flask, 2-hydroxyethyl methacrylate (HEMA, 10.3 g, 0.09 mol), acrylic acid (AA, 2.2 g, 0.03 mol), dimethyl sulfoxide (49.7 g), polymerization initiator VA-061 (Wako Pure Chemical Industries, Ltd., 0.009 g, 0.038 mmol) and 2-mercaptoethanol (2-ME, 2.6 µL, 0.038 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 60° C. for 0.5 hours, followed by temperature rise to 70° C. and further stirring for 4.5 hours. After completion of the polymerization, the polymerization reaction solution was cooled to room temperature and 20 mL of ethanol was added, and then the mixed solution was poured into 500 mL of water and left to stand overnight. On the next day, the supernatant was discarded and the obtained solid component was further washed twice with 500 mL of water. The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 83 kD, Mw: 188 kD (Mw/Mn=2.3).

Synthesis Example 23

CPHA: 2-Hydroxyethyl Methacrylate/Acrylic Acid (Molar Ratio of 3/1)

In a 300 mL three-necked flask, 2-hydroxyethyl methacrylate (HEMA, 10.3 g, 0.09 mol), acrylic acid (AA, 2.2 g, 0.03 mol), dimethyl sulfoxide (49.8 g), a polymerization initiator VA-061 (Wako Pure Chemical Industries, Ltd., 0.009 g, 0.038 mmol), 2-mercaptoethanol (2-ME, 7.8 µL, 0.111 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 60° C. for 0.5 hours, followed by temperature rise to 70° C. and further stirring for 4.5 hours. After completion of the polymerization, the polymerization reaction solution was cooled to room temperature and 20 mL of ethanol was added, and then the mixed solution was poured into 500 mL of water and left to stand overnight. On the next day, the supernatant was discarded and the obtained solid component was further washed twice with 500 mL of water. The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 50 kD, Mw: 96 kD (Mw/Mn=1.9).

Synthesis Example 24

CPHA: 2-Hydroxyethyl Methacrylate/Acrylic Acid (Molar Ratio of 1/1)

In a 200 mL three-necked flask, 2-hydroxyethyl methacrylate (HEMA, 11.4 g, 0.10 mol), acrylic acid (AA, 7.21 g, 0.10 mol), dimethyl sulfoxide (74.5 g) and a polymerization initiator VA-061 (Wako Pure Chemical Industries, Ltd., 0.016 g, 0.062 mmol) were charged, and then equipped with a three-way stop-cock, a reflux condenser tube, a thermometer and a mechanical stirrer. The concentration of the monomer was 20% by weight. After degassing inside the three-necked flask using a vacuum pump and repeating replacement by argon three times, stirring was carried out at 60° C. for 0.5 hours, followed by temperature rise to 70° C. and further stirring for 6.5 hours. After completion of the polymerization, the polymerization reaction solution was cooled to room temperature, and then the mixed solution was poured into water (1,000 mL)/ethanol (10 mL) and left to stand overnight. On the next day, the supernatant was discarded and the obtained solid component was further washed twice with 700 mL of water. The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 79 kD, Mw: 226 kD (Mw/Mn=2.9).

Reference Example 38

Hereinafter, pure water means water purified by filtering through a reverse osmosis membrane.
Preparation of Coating Solution
<PEI Solution A>
Polyethyleneimine (P3143, Sigma-Aldrich Corporation, molecular weight of 750,000) was dissolved in pure water to obtain an aqueous 1% by weight solution.
<PEI Solution B>
Polyethyleneimine (P-70, 167-11951, Wako Pure Chemical Industries, Ltd., molecular weight of 70,000) was dissolved in pure water to obtain an aqueous 1% by weight solution.
<PAA Solution>
Polyacrylic acid (169-18591, Wako Pure Chemical Industries, Ltd., molecular weight 250,000) was dissolved in pure water to obtain an aqueous 1.2% by weight solution.
<PAAM Solution A>
Polyallylamine (PAA-15C, Nitto Boseki Co., Ltd., molecular weight 15,000) was dissolved in pure water to obtain an aqueous 1% by weight solution.
<PAAM Solution B>
Polyallylamine (PAA-25, Nitto Boseki Co., Ltd., molecular weight 25,000) was dissolved in pure water to obtain an aqueous 1% by weight solution.
<PAS Solution>
A diallyldimethylammonium chloride polymer (PAS-H-10L, Nitto Boseki Co., Ltd., molecular weight of 200,000) was dissolved in pure water to obtain an aqueous 1% by weight solution
<Solution of Copolymer>
The copolymers obtained in the Synthesis Examples shown in Table 6 were respectively dissolved in the solvents shown in Table 6 to obtain solutions having each concentration shown in Table 6.

TABLE 6

| Copolymer | | Copolymerization monomer A | Copolymerization monomer B | A (Molar ratio) | B (Molar ratio) | Mn (kD) | Mw (kD) | Solvent | Solution concentration (% by weight) |
|---|---|---|---|---|---|---|---|---|---|
| CPVPA solution A | Synthesis Example 1 | NVP | AA | 2 | 1 | 46 | 180 | Pure water | 1 |
| CPVPA solution B | Synthesis Example 2 | NVP | AA | 1 | 2 | 65 | 202 | Pure water | 1 |
| CPVPA solution C | Synthesis Example 3 | NVP | AA | 90 | 10 | 35 | 130 | Pure water | 1 |
| CPVPA solution D | Synthesis Example 4 | NVP | AA | 80 | 20 | 45 | 193 | Pure water | 1 |
| CPDA solution A | Synthesis Example 5 | DMA | AA | 2 | 1 | 55 | 192 | Pure water | 1 |
| CPDA solution B | Synthesis Example 6 | DMA | AA | 1 | 2 | 87 | 235 | Pure water | 1 |
| CPDA solution C | Synthesis Example 7 | DMA | AA | 90 | 10 | 54 | 162 | Pure water | 1 |
| CPDA solution D | Synthesis Example 8 | DMA | AA | 95 | 5 | 77 | 229 | Pure water | 1 |
| CPDA solution E | Synthesis Example 9 | DMA | AA | 80 | 20 | 80 | 227 | Pure water | 1 |
| CPDA solution F | Synthesis Example 10 | DMA | AA | 50 | 50 | 84 | 195 | Pure water | 1 |
| CPDA solution G | Synthesis Example 11 | DMA | AA | 95 | 5 | 139 | 423 | Pure water | 1 |
| CPDA solution H | Synthesis Example 12 | DMA | AA | 80 | 20 | 114 | 442 | Pure water | 1 |
| CPDA solution I | Synthesis Example 13 | DMA | AA | 50 | 50 | 148 | 472 | Pure water | 1 |

TABLE 6-continued

| | Copolymer | Copolymerization monomer A | Copolymerization monomer B | A (Molar ratio) | B (Molar ratio) | Mn (kD) | Mw (kD) | Solvent | Solution concentration (% by weight) |
|---|---|---|---|---|---|---|---|---|---|
| CPDA solution J | Synthesis Example 14 | DMA | AA | 95 | 5 | 190 | 609 | Pure water | 1 |
| CPDA solution K | Synthesis Example 15 | DMA | AA | 80 | 20 | 169 | 537 | Pure water | 1 |
| CPDA solution L | Synthesis Example 16 | DMA | AA | 50 | 50 | 124 | 552 | Pure water | 1 |
| CPDEAC solution | Synthesis Example 17 | DEAA | ACMO | 50 | 50 | 49 | 162 | Pure water | 1 |
| CPACDM solution | Synthesis Example 18 | ACMO | DMA | 50 | 50 | 4.3 | 17 | Pure water | 1 |
| CPDEDM solution | Synthesis Example 19 | DEAA | DMA | 50 | 50 | 90 | 327 | Pure water | 1 |
| CPHEDM solution | Synthesis Example 20 | HEAA | DMA | 50 | 50 | 109 | 660 | Pure water | 1 |
| CPHA solution A | Synthesis Example 21 | HEMA | AA | 3 | 1 | 61 | 267 | Aqueous 0.5 wt % methanol solution | 0.1 |
| CPHA solution B | Synthesis Example 22 | HEMA | AA | 3 | 1 | 83 | 188 | Aqueous 0.5 wt % methanol solution | 0.1 |
| CPHA solution C | Synthesis Example 23 | HEMA | AA | 3 | 1 | 50 | 96 | Aqueous 0.5 wt % methanol solution | 0.1 |
| CPHA solution D | Synthesis Example 24 | HEMA | AA | 1 | 1 | 79 | 226 | Aqueous 0.5 wt % methanol solution | 0.1 |
| CPHA solution E | Synthesis Example 23 | HEMA | AA | 3 | 1 | 50 | 96 | Aqueous 0.5 wt % methanol solution | 0.01 |
| CPHA solution F | Synthesis Example 23 | HEMA | AA | 3 | 1 | 50 | 96 | Aqueous 5 wt % methanol solution | 1 |

NVP: N-vinylpyrrolidone
DMA: N,N-dimethylacrylamide
DEAR: N,N-diethylacrylamide
ACMO: Acryloylmorpholine
HEAA: N-(2-hydroxyethyl)acrylamide
HEMA: 2-hydroxyethyl methacrylate
AA: Acrylic acid <Other Solutions>

The substances shown in Table 7 were respectively dissolved in pure water to obtain aqueous solutions having each concentration shown in Table 7.

TABLE 7

| | Name of substance | Mw (kD) | Solution concentration (% by weight) |
|---|---|---|---|
| PEI solution A | Polyethyleneimine | 750 | 1 |
| PEI solution B | Polyethyleneimine | 70 | 1 |
| PAA solution | Polyacrylic acid | 250 | 1.2 |
| PAAM solution A | Polyallylamine | 15 | 1 |
| PAAM solution B | Polyallylamine | 25 | 1 |
| PAS solution | Diallyldimethylammonium chloride polymer | 200 | 1 |
| PVP solution | Polyvinylpyrrolidone (K90) | 300 | 1 |
| PDMAA solution | Poly(N,N-dimethylacrylamide) | 400 | 1 |
| VA64 solution | Vinylpyrrolidone/vinyl acetate (60/40) copolymer | 190 | 1 |
| PACMO solution | Polyacryloylmorpholine | 243 | 1 |
| PDEAA solution | Poly(N,N-diethylacrylamide) | 47 | 1 |
| PDMAA solution | Poly(N-methoxymethylacrylamide) | 17 | 1 |
| PHMAA solution | Poly(N-hydroxymethylacrylamide) | 148 | 1 |
| PNVF solution | Poly(N-vinylformamide) | 183 | 1 |
| PHEAA solution | Poly[N-(2-hydroxyethyl)acrylamide] | 88 | 1 |
| AcOH solution | Acetic acid | — | 1 |
| DEA solution | Diethylamine | — | 1 |
| AP solution A | Hyaluronic acid Na | 1,190 | 0.1 |
| AP solution B | KIMICA ALGIN I-3 | 349 | 0.1 |
| AP solution C | Alginic acid ester HV | 328 | 0.1 |
| AP solution D | NS-300 (Carmellose) | 12,000 | 0.1 |
| AP solution E | SUNROSE (APP-84) | 543 | 0.1 |
| AP solution F | Chondroitin sulfate Na | 25 | 0.1 |
| AP solution G | GLYLOID 6C | 500 | 0.1 |
| AP solution H | Rhaball gum CG-SFT | 5,340 | 0.1 |
| AP solution I | APP-84 | 543 | 1 |

Hyaluronic acid Na: Sodium hyaluronate (CHA) (CHISSO CORPORATION)
KIMICA ALGIN I-3: Sodium alginate (KIMICA Corporation)
KIMILOID HV: Alginic acid propylene glycol ester (KIMICA corporation)
NS-300 (Carmellose): Carboxymethyl cellulose (GOTOKU CHEMICAL COMPANY LTD.)
SUNROSE (APP-84): Carboxymethyl cellulose (NIPPON PAPER Chemicals CO., LTD.)
Chondroitin sulfate Na: Chondroitin sulfate sodium (SEIKAGAKU CORPORATION)
GLYLOID 6C: Tamarind gum (Dainippon Sumitomo Pharma Co., Ltd.) Rhaball gum CG-SFT: Xanthan gum (Dainippon Sumitomo Pharma Co., Ltd.).

Examples 1 to 3

The moldings obtained in the respective Reference Examples shown in Table 8 were immersed in a PEI solution A for 30 minutes and then respectively immersed in three pure water baths for 5 minutes. The moldings were immersed in a PAA solution for 30 minutes and then respectively immersed in three pure water baths for 5 minutes. Wettability and dynamic contact angle of the obtained low water content soft contact lenses were evaluated. The results are shown in Table 8. The reference sign "-" in the table means that a coating operation using a solution is not carried out.

Examples 4 to 6

The moldings obtained in the respective Reference Examples shown in Table 8 were immersed in a PAA solution for 30 minutes and then respectively immersed in three pure water baths for 5 minutes. The moldings were immersed in a PEI solution A for 30 minutes and then respectively immersed in three pure water baths for 5 minutes. The moldings were immersed in a PAA solution for 30 minutes and then respectively immersed in three pure water baths for 5 minutes. Wettability and dynamic contact angle of the obtained low water content soft contact lenses were evaluated. The results are shown in Table 8.

Examples 7 to 14

The moldings obtained in the respective Reference Examples shown in Table 8 were immersed in a first solution for 30 minutes and then respectively immersed in three pure water baths for 5 minutes. The moldings were immersed in a second solution for 30 minutes and then respectively immersed in three pure water baths for 5 minutes. The moldings were immersed in a PAA solution for 30 minutes and then respectively immersed in three pure water baths for 5 minutes. Wettability and dynamic contact angle of the obtained low water content soft contact lenses were evaluated. The results are shown in Table 8.

Comparative Examples 1 to 3

Wettability and dynamic contact angle of the moldings obtained in the respective Reference Examples shown in Table 8 were evaluated. The results are shown in Table 8. The reference sign "-" in the table means that a coating operation using a solution is not carried out.

Comparative Examples 4 to 6

The moldings obtained in the respective Reference Examples shown in Table 8 were immersed in a PEI solution A for 30 minutes and then respectively immersed in three pure water baths for 5 minutes. Wettability and dynamic contact angle of the obtained low water content soft contact lenses were evaluated. The results are shown in Table 8. The reference sign "-" in the table means that a coating operation using a solution is not carried out.

Comparative Examples 7 to 9

The moldings obtained in the respective Reference Examples shown in Table 8 were immersed in a PAA solution for 30 minutes and then respectively immersed in three pure water baths for 5 minutes. Wettability and dynamic contact angle of the obtained low water content soft contact lenses were evaluated. The results are shown in Table 8. The reference sign "-" in the table means that a coating operation using a solution is not carried out.

TABLE 8

| | Molding subjected to coating | First solution | Second solution | Third solution | Wettability | Dynamic contact angle (Advance) |
|---|---|---|---|---|---|---|
| Example 1 | Reference Example 4 | PEI solution A | PAA solution | — | A | Unevaluated |
| Example 2 | Reference Example 16 | PEI solution A | PAA solution | — | A | Unevaluated |
| Example 3 | Reference Example 22 | PEI solution A | PAA solution | — | A | Unevaluated |
| Example 4 | Reference Example 4 | PAA solution | PEI solution A | PAA solution | A | 65 |
| Example 5 | Reference Example 16 | PAA solution | PEI solution A | PAA solution | A | 59 |
| Example 6 | Reference Example 22 | PAA solution | PEI solution A | PAA solution | A | 54 |
| Example 7 | Reference Example 4 | PAA solution | PAS solution | PAA solution | A | Unevaluated |
| Example 8 | Reference Example 4 | PAA solution | PAAM solution A | PAA solution | A | Unevaluated |
| Example 9 | Reference Example 4 | PAA solution | PAAM solution B | PAA solution | A | Unevaluated |
| Example 10 | Reference Example 4 | PAA solution | PEI solution B | PAA solution | A | Unevaluated |
| Example 11 | Reference Example 22 | PAA solution | PAS solution | PAA solution | A | Unevaluated |
| Example 12 | Reference Example 22 | PAA solution | PAAM solution A | PAA solution | A | Unevaluated |
| Example 13 | Reference Example 22 | PAA solution | PAAM solution B | PAA solution | A | Unevaluated |
| Example 14 | Reference Example 22 | PAA solution | PEI solution B | PAA solution | A | Unevaluated |
| Comparative Example 1 | Reference Example 4 | — | — | — | E | 115 |
| Comparative Example 2 | Reference Example 16 | — | — | — | E | 118 |
| Comparative Example 3 | Reference Example 22 | — | — | — | E | 113 |
| Comparative Example 4 | Reference Example 4 | PEI solution A | — | — | E | Unevaluated |
| Comparative Example 5 | Reference Example 16 | PEI solution A | — | — | E | Unevaluated |
| Comparative Example 6 | Reference Example 22 | PEI solution A | — | — | E | Unevaluated |
| Comparative Example 7 | Reference Example 4 | PAA solution | — | — | E | Unevaluated |
| Comparative Example 8 | Reference Example 16 | PAA solution | — | — | E | Unevaluated |
| Comparative Example 9 | Reference Example 22 | PAA solution | — | — | E | Unevaluated |

Reference Examples 39 to 42

In the very same manner as in Reference Example 1, except that polydimethylsiloxane having a methacryloyl group at both ends (DMS-R31, Gelest, Inc., below-mentioned compound of the formula (M2), number average molecular weight of 13,000) (50 parts by weight) was used as a component A, and that a monomer having a fluoroalkyl group shown in Table 9 (50 parts by weight) was used as a component B, a low water content soft contact lenses were obtained. The evaluation results of the obtained low water content soft contact lenses are shown in Table 9.

weight isopropyl alcohol solution and a contact lens-shaped molding was removed from the mold. The obtained molding was immersed in a large excess amount of an aqueous 80% by weight isopropyl alcohol solution at 60° C. for 2 hours. Furthermore, the molding was immersed in a large excess amount of an aqueous 50% by weight isopropyl alcohol solution at room temperature for 30 minutes, followed by immersion in a large excess amount of an aqueous 25% by weight isopropyl alcohol solution at room temperature for 30 minutes, and further immersion in a large excess amount of pure water at room temperature for 30 minutes. Finally, the molding immersed in clean pure water was put in a closed vial

TABLE 9

| | Component A | Component B | | Si atom | Evaluation results | | |
|---|---|---|---|---|---|---|---|
| | | | | | Transparency | Elongation | Folding resistance |
| | DMS-R31 (Parts by weight) | Name | (Parts by weight) | content (% by weight) | | (number of specimens which were not broken) | |
| Reference Example 39 | 50 | Biscoat 3FM | 50 | 19 | A | 4 | B |
| Reference Example 40 | 50 | Biscoat 8F | 50 | 19 | B | 3 | B |
| Reference Example 41 | 50 | Biscoat 17F | 50 | 19 | *1 | *1 | *1 |
| Reference Example 42 | 50 | HFIP-M | 50 | 19 | A | 4 | A |

*1: abandoned polymerization because of phase separation of polymerization raw solution
Biscoat 3FM: Trifluoroethyl methacrylate (Osaka Organic Chemical Industry Ltd.)
Biscoat 8F: Octafluoropentyl acrylate (Osaka Organic Chemical Industry Ltd.)
Biscoat 17F: Heptadecafluorodecyl acrylate (Osaka Organic Chemical Industry Ltd.)
HFIP-M: Hexafluoroisopropyl methacrylate (Central Glass Co., Ltd.).

Reference Example 43

Polydimethylsiloxane having a methacryloyl group at both ends (DMS-R31, Gelest, Inc., below-mentioned compound of the formula (M2), number average molecular weight of 30,000) (50 parts by weight) as a component A, trifluoroethyl acrylate (Biscoat 3F, Osaka Organic Chemical Industry Ltd.) (46 parts by weight) as a component B, methyl methacrylate (3 parts by weight) as a component C, an ultraviolet absorber having a polymerizable group (RUVA-93, compound represented by the formula (M1), Otsuka Chemical Co., Ltd.) (1 part by weight) as a component C, a polymerization initiator-"IRGACURE®" 1850 (Ciba Specialty Chemicals Inc., 2 parts by weight) and t-amyl alcohol (10 parts by weight) were mixed and then stirred. As a result, a uniform and transparent monomer mixture was obtained. This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. In a glove box under a nitrogen atmosphere, the monomer mixture was injected into a mold for contact lens made of a transparent resin (poly-4-methylpentene-1) and then polymerized by irradiating with light (8,000 lux, 20 minutes) using a fluorescent lamp (Toshiba Corporation, FL-6D, quasi-daylight, 6W, 4 lamps). After polymerization, the whole mold was immersed in an aqueous 60% by bottle, and then autoclave sterilization was carried out at 121° C. for 30 minutes. The obtained molding had a water content of less than 1%. Using two glass plates and a gasket as a mold, a film-shaped sample measuring 60 mm×60 mm×0.25 mm was obtained.

[Chemical Formula 3]

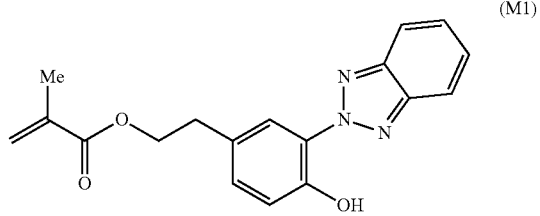

(M1)

Reference Examples 44 to 47 and 70 to 75

In the same manner as in Reference Example 43, except that the components shown in Table 10 were used, contact lens-shaped moldings, and film-shaped samples each measuring 60 mm×60 mm×0.25 mm were obtained. The reference sign "-" in the table means that the component is not used.

TABLE 10

| | Component A | | Component B | | Component C | | Component C | |
|---|---|---|---|---|---|---|---|---|
| | Name | Parts by weight | Name | Parts by weight | Name | Parts by weight | Name | Parts by weight |
| Reference Example 43 | DMS-R31 | 50 | Biscoat 3F | 46 | MMA | 3 | — | — |
| Reference Example 44 | FM-7726 | 50 | Biscoat 3F | 46 | MMA | 3 | — | — |
| Reference Example 45 | FM-7726L | 50 | Biscoat 3F | 46 | MMA | 3 | — | — |
| Reference Example 46 | X-22-164C | 50 | Biscoat 3F | 46 | MMA | 3 | — | — |
| Reference Example 47 | DMS-R22 | 50 | Biscoat 3F | 46 | MMA | 3 | — | — |
| Reference Example 48 | FM-7726 | 49 | Biscoat 3F | 45 | EHMA | 5 | DMAA | 1 |
| Reference Example 49 | FM-7726 | 47 | Biscoat 3F | 45 | EHMA | 5 | DMAA | 3 |
| Reference Example 50 | FM-7726 | 45 | Biscoat 3F | 45 | EHMA | 5 | DMAA | 5 |
| Reference Example 51 | FM-7726 | 42 | Biscoat 3F | 45 | EHMA | 5 | DMAA | 8 |
| Reference Example 52 | FM-7726 | 49 | Biscoat 3F | 45 | EHMA | 5 | DMAEA | 1 |
| Reference Example 53 | FM-7726 | 47 | Biscoat 3F | 45 | EHMA | 5 | DMAEA | 3 |
| Reference Example 54 | FM-7726 | 42 | Biscoat 3F | 45 | EHMA | 5 | DMAEA | 8 |
| Reference Example 55 | FM-7726 | 49 | Biscoat 3F | 45 | EHMA | 5 | DMAPAA | 1 |
| Reference Example 56 | FM-7726 | 47 | Biscoat 3F | 45 | EHMA | 5 | DMAPAA | 3 |
| Reference Example 57 | FM-7726 | 42 | Biscoat 3F | 45 | EHMA | 5 | DMAPAA | 8 |
| Reference Example 58 | FM-7726 | 49 | Biscoat 3F | 45 | EHMA | 5 | DEAEMA | 1 |
| Reference Example 59 | FM-7726 | 47 | Biscoat 3F | 45 | EHMA | 5 | DEAEMA | 3 |
| Reference Example 60 | FM-7726 | 42 | Biscoat 3F | 45 | EHMA | 5 | DEAEMA | 8 |
| Reference Example 61 | FM-7726 | 49 | Biscoat 3F | 45 | EHMA | 5 | AA | 1 |
| Reference Example 62 | FM-7726 | 47 | Biscoat 3F | 45 | EHMA | 5 | AA | 3 |
| Reference Example 63 | FM-7726 | 42 | Biscoat 3F | 45 | EHMA | 5 | AA | 8 |
| Reference Example 64 | FM-7726 | 49 | Biscoat 3F | 45 | EHMA | 5 | MAA | 1 |
| Reference Example 65 | FM-7726 | 47 | Biscoat 3F | 45 | EHMA | 5 | MAA | 3 |
| Reference Example 66 | FM-7726 | 42 | Biscoat 3F | 45 | EHMA | 5 | MAA | 8 |
| Reference Example 67 | DMS-R31 | 50 | Biscoat 3F | 46 | MMA | 3 | — | — |
| Reference Example 68 | FM-7726 | 50 | Biscoat 3F | 46 | MMA | 3 | — | — |
| Reference Example 69 | FM-7726L | 50 | Biscoat 3F | 46 | MMA | 3 | — | — |
| Reference Example 70 | FM-7726 | 50 | Biscoat 3F | 46 | MMA | 3 | — | — |
| Reference Example 71 | DMS-R31 | 50 | Biscoat 3F | 46 | MMA | 3 | — | — |
| Reference Example 72 | DMS-R31 | 50 | Biscoat 3F | 46 | MMA | 3 | — | — |
| Reference Example 73 | DMS-R31 | 50 | Biscoat 3F | 46 | MMA | 3 | — | — |
| Reference Example 74 | FM-7726 | 50 | Biscoat 3F | 46 | MMA | 3 | — | — |
| Reference | FM-7726L | 50 | Biscoat 3F | 46 | MMA | 3 | — | — |

TABLE 10-continued

| | Component C Ultraviolet absorber | Component C Colorant | Polymerization initiator | | Solvent | | Si atom |
|---|---|---|---|---|---|---|---|
| | RUVA-93 (Parts by weight) | Uniblue A (Parts by weight) | Name | Parts by weight | Name | Parts by weight | content (% by weight) |
| Reference Example 43 | 1 | — | IRGACURE 1850 | 1 | TAA | 10 | 19 |
| Reference Example 44 | 1 | — | IRGACURE 1850 | 1 | TAA | 10 | 19 |
| Reference Example 45 | 1 | — | IRGACURE 1850 | 1 | TAA | 10 | 19 |
| Reference Example 46 | 1 | — | IRGACURE 1850 | 1 | TAA | 10 | 18 |
| Reference Example 47 | 1 | — | IRGACURE 1850 | 1 | TAA | 10 | 18 |
| Reference Example 48 | 1 | 0.1 | IRGACURE 819 | 0.5 | TAA | 10 | 18 |
| Reference Example 49 | 1 | 0.1 | IRGACURE 819 | 0.5 | TAA | 10 | 18 |
| Reference Example 50 | 1 | 0.1 | IRGACURE 819 | 0.5 | TAA | 10 | 17 |
| Reference Example 51 | 1 | 0.1 | IRGACURE 819 | 0.5 | TAA | 10 | 16 |
| Reference Example 52 | 1 | 0.1 | IRGACURE 819 | 0.5 | TAA | 10 | 18 |
| Reference Example 53 | 1 | 0.1 | IRGACURE 819 | 0.5 | TAA | 10 | 18 |
| Reference Example 54 | 1 | 0.1 | IRGACURE 819 | 0.5 | TAA | 10 | 16 |
| Reference Example 55 | 1 | 0.1 | IRGACURE 819 | 0.5 | TAA | 10 | 18 |
| Reference Example 56 | 1 | 0.1 | IRGACURE 819 | 0.5 | TAA | 10 | 18 |
| Reference Example 57 | 1 | 0.1 | IRGACURE 819 | 0.5 | TAA | 10 | 16 |
| Reference Example 58 | 1 | 0.1 | IRGACURE 819 | 0.5 | TAA | 10 | 18 |
| Reference Example 59 | 1 | 0.1 | IRGACURE 819 | 0.5 | TAA | 10 | 18 |
| Reference Example 60 | 1 | 0.1 | IRGACURE 819 | 0.5 | TAA | 10 | 16 |
| Reference Example 61 | 1 | 0.1 | IRGACURE 819 | 0.5 | TAA | 10 | 18 |
| Reference Example 62 | 1 | 0.1 | IRGACURE 819 | 0.5 | TAA | 10 | 18 |
| Reference Example 63 | 1 | 0.1 | IRGACURE 819 | 0.5 | TAA | 10 | 16 |
| Reference Example 64 | 1 | 0.1 | IRGACURE 819 | 0.5 | TAA | 10 | 18 |
| Reference Example 65 | 1 | 0.1 | IRGACURE 819 | 0.5 | TAA | 10 | 18 |
| Reference Example 66 | 1 | 0.1 | IRGACURE 819 | 0.5 | TAA | 10 | 16 |
| Reference Example 67 | 1 | 0.1 | IRGACURE 819 | 0.5 | TAA | 10 | 19 |
| Reference Example 68 | 1 | 0.1 | IRGACURE 819 | 0.5 | TAA | 10 | 19 |
| Reference Example 69 | 1 | 0.1 | IRGACURE 819 | 0.5 | TAA | 10 | 19 |
| Reference Example 70 | 1 | — | IRGACURE 819 | 2 | TAA | 10 | 19 |
| Reference Example 71 | 1 | — | IRGACURE 819 | 2 | TAA | 10 | 19 |
| Reference Example 72 | 1 | — | IRGACURE 1850 | 1 | TAA | 20 | 19 |
| Reference Example 73 | 1 | — | IRGACURE 819 | 0.25 | TAA | 20 | 19 |
| Reference Example 74 | 1 | — | IRGACURE 819 | 0.25 | TAA | 20 | 19 |
| Reference | 1 | — | IRGACURE | 0.25 | TAA | 20 | 19 |

DMS-R31: Compound of the formula (M2), Mw 30 kD, Mn 13 kD, Gelest, Inc.
FM-7726: Compound of the formula (M2), Mw: 29 kD, Mn: 26 kD, CHISSO CORPORATION
FM-7726L: Compound of the formula (M2), Mw: 31 kD, Mn: 20 kD, CHISSO CORPORATION
X-22-164C: Compound of the formula, (M2) Mw: 7.2 kD, Mn: 4.8 kD, Shin-Etsu Chemical Co. Ltd.
DMS-R22: Compound of the formula (M2), Mw: 8.3 kD, Mn: 7.4 kD, Gelest, Inc.

In the formula (M2), n represents the number of repeating units and is determined by the molecular weight of the compound.

[Chemical Formula 4]

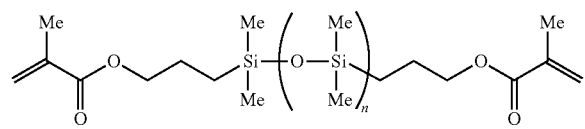

(M2)

Biscoat 3F: Trifluoroethyl acrylate
MMA: Methyl methacrylate
EHMA: 2-ethylhexyl acrylate
DMAA: N,N-dimethylacrylamide
DMAEA: N,N-dimethylaminoethyl acrylate
DMAPAA: N,N-diethylaminopropyl acrylamide
DEAEMA: N,N-diethylaminoethyl methacrylate
TAA: t-amyl alcohol
AA: Acrylic acid
MAA: Methacrylic acid Reference Example 48

Polydimethylsiloxane having a methacryloyl group at both ends (FM7726, CHISSO CORPORATION, above-mentioned compound of the formula (M2), weight average molecular weight of 29 kD, number average molecular weight of 26 kD) (49 parts by weight) as a component A, trifluoroethyl acrylate (Biscoat 3F, Osaka Organic Chemical Industry Ltd.) (45 parts by weight) as a component B, 2-ethylhexyl acrylate (5 parts by weight) as a component C, N,N-dimethylacrylamide (1 part by weight) as a component C, an ultraviolet absorber having a polymerizable group (RUVA-93, Otsuka Chemical Co., Ltd.) (1 part by weight) as a component C, a colorant having a polymerizable group [(Uniblue A, Sigma-Aldrich Corporation, formula (M3)] (0.1 part by weight) as a component C, a polymerization initiator "IRGA-CURE®" 819 (Ciba Specialty Chemicals Inc., 0.75 part by weight) and t-amyl alcohol (10 parts by weight) were mixed and then stirred. The mixture was filtered through a membrane filter (0.45 μm) to remove insoluble matters, and thus a monomer mixture was obtained. This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. In a glove box under a nitrogen atmosphere, the monomer mixture was injected into a mold for contact lens made of a transparent resin (poly-4-methylpentene-1) and then polymerized by irradiating with light (8,000 lux, 20 minutes) using a fluorescent lamp (Toshiba Corporation, FL-6D, quasi-daylight, 6W, 4 lamps). After polymerization, the whole mold was immersed in an aqueous 60% by weight isopropyl alcohol solution and a contact lens-shaped molding was removed from the mold. The obtained molding was immersed in a large excess amount of an aqueous 80% by weight isopropyl alcohol solution at 60° C. for 2 hours. Furthermore, the molding was immersed in a large excess amount of an aqueous 50% by weight isopropyl alcohol solution at room temperature for 30 minutes, followed by immersion in a large excess amount of an aqueous 25% by weight isopropyl alcohol solution at room temperature for 30 minutes, and further immersion in a large excess amount of pure water at room temperature for 30 minutes. Finally, the molding immersed in clean pure water was put in a closed vial bottle, and then autoclave sterilization was carried out at 121° C. for 30 minutes. The obtained molding had a water content of less than 1%. Using two glass plates and a gasket as a mold, a film-shaped sample measuring 60 mm×60 mm×0.25 mm was obtained.

[Chemical Formula 5]

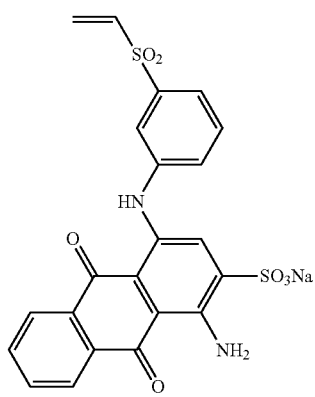

(M3)

Reference Examples 49 to 69

In the same manner as in Reference Example 48, except that the components shown in Table 10 were used, contact lens-shaped moldings, and film-shaped samples each measuring 60 mm×60 mm×0.25 mm were obtained. The reference sign "-" in the table means that the component is not used.

Examples 15 to 183, Comparative Examples 10 to 30 and Control Example 1 and 2

The moldings or commercially available contact lenses obtained in the respective Reference Examples shown in Tables 11 to 16 were immersed in a first solution shown in Tables 11 to 16 for 30 minutes and then respectively immersed in three pure water baths for 5 minutes. The moldings or commercially available contact lens were immersed in a second solution shown in Tables 11 to 16 for 30 minutes and then respectively immersed in three pure water baths for 5 minutes. The above-mentioned operations were similarly repeated with respect to third to fifth solutions. The evaluation of the obtained low water content soft contact lens was carried out. The results are shown in Tables 11 to 16. The reference sign "-" in the table means that a coating operation using a solution is not carried out, or the evaluation is not carried out.

Control Examples are commercially available silicone hydrogel soft contact lenses and have a problem that wearers often feel dry, while other physical properties are almost satisfactory. Therefore, it is preferred that the respective physical properties of the low water content soft contact lenses of the present invention are equal or superior to those of Control Examples.

TABLE 11-1

| | Molding subjected to coating | First solution | Second solution | Third solution | Wett-ability | Dynamic contact angle (Advance) | Friction (gf) | Lubricity | Adhesion of mucin (µg/cm²) | Adhesion of lipid |
|---|---|---|---|---|---|---|---|---|---|---|
| Example 15 | Reference Example 46 | PAA solution | PEI solution A | — | B | 60 | 61 | C | 2.7 | — |
| Example 16 | Reference Example 46 | PAA solution | PEI solution A | PAA solution | A | 36 | 42 | C | 3.4 | D |
| Example 17 | Reference Example 46 | PAA solution | PEI solution A | CPDA solution B | B | 34 | 22 | A | 6.0 | — |
| Example 18 | Reference Example 46 | PAA solution | PEI solution A | CPDA solution A | B | 32 | 20 | A | 1.8 | — |
| Example 19 | Reference Example 46 | PAA solution | PEI solution A | CPDA solution C | C | 39 | 46 | A | 2.3 | — |
| Example 20 | Reference Example 46 | PAA solution | PEI solution A | CPDA solution D | C | 41 | 25 | A | 5.1 | — |
| Example 21 | Reference Example 46 | PAA solution | PEI solution A | CPDA solution E | C | 24 | 29 | A | 3.2 | — |
| Example 22 | Reference Example 46 | PAA solution | PEI solution A | CPDA solution F | A | 29 | 14 | A | 3.0 | — |
| Example 23 | Reference Example 46 | PAA solution | PEI solution A | CPDA solution G | C | 52 | 18 | A | 3.0 | — |
| Example 24 | Reference Example 46 | PAA solution | PEI solution A | CPDA solution H | B | 20 | 16 | A | 3.3 | — |
| Example 25 | Reference Example 46 | PAA solution | PEI solution A | CPDA solution I | A | 16 | 14 | A | 3.9 | — |
| Example 26 | Reference Example 46 | PAA solution | PEI solution A | CPDA solution J | C | 42 | 23 | A | 3.5 | — |
| Example 27 | Reference Example 46 | PAA solution | PEI solution A | CPDA solution K | C | 31 | 19 | A | 3.4 | — |
| Example 28 | Reference Example 46 | PAA solution | PEI solution A | CPDA solution L | A | 16 | 19 | A | 3.9 | — |
| Example 29 | Reference Example 46 | PAA solution | PEI solution A | AP solution A | B | 26 | 55 | C | 2.4 | — |
| Example 30 | Reference Example 46 | PAA solution | PEI solution A | AP solution B | B | 25 | 53 | C | 2.3 | — |
| Example 31 | Reference Example 46 | PAA solution | PEI solution A | AP solution C | B | 22 | 47 | C | 2.6 | — |
| Example 32 | Reference Example 46 | PAA solution | PEI solution A | AP solution D | A | 41 | 61 | C | 3.1 | — |
| Example 33 | Reference Example 46 | PAA solution | PEI solution A | AP solution E | A | 25 | 71 | C | 1.9 | — |
| Example 34 | Reference Example 46 | PAA solution | PEI solution A | AP solution F | B | 57 | 57 | C | 2.7 | — |
| Example 35 | Reference Example 46 | PAA solution | PEI solution A | AP solution G | B | 53 | 63 | C | 2.8 | — |
| Example 36 | Reference Example 46 | PAA solution | PEI solution A | AP solution H | B | 50 | 49 | C | 2.9 | — |
| Example 37 | Reference Example 46 | PAA solution | PEI solution A | AP solution I | A | 47 | 55 | C | 2.5 | — |
| Example 38 | Reference Example 46 | PAA solution | PEI solution A | PVP solution | B | 53 | 57 | D | 2.7 | — |
| Example 39 | Reference Example 46 | PAA solution | PEI solution A | VA64 solution | C | 83 | 59 | D | 3.0 | — |
| Example 40 | Reference Example 46 | PAA solution | PEI solution A | PDMAA solution | C | 49 | 66 | D | 3.9 | — |
| Example 41 | Reference Example 46 | PAA solution | PEI solution A | PACMO solution | A | 45 | 59 | D | 3.8 | — |
| Example 42 | Reference Example 46 | PAA solution | PEI solution A | PDEAA solution | C | 66 | 60 | D | 4.4 | — |
| Example 43 | Reference Example 46 | PAA solution | PEI solution A | PMMAA solution | C | 85 | 74 | D | 3.6 | — |
| Example 44 | Reference Example 46 | PAA solution | PEI solution A | PHMAA solution | B | 59 | 69 | D | 3.2 | — |
| Example 45 | Reference Example 46 | PAA solution | PEI solution A | PNVF solution | A | 37 | 68 | D | 3.2 | — |
| Example 46 | Reference Example 46 | PAA solution | PEI solution A | PHEAA solution | B | 51 | 73 | D | 3.9 | — |
| Example 47 | Reference Example 46 | PAA solution | PEI solution A | CPDEAC solution | B | 60 | 63 | D | 3.4 | — |
| Example 48 | Reference Example 46 | PAA solution | PEI solution A | CPACDM solution | A | 26 | 64 | D | 3.7 | — |
| Example 49 | Reference Example 46 | PAA solution | PEI solution A | CPDEDM solution | C | 76 | 54 | D | 3.7 | — |
| Example 50 | Reference Example 46 | PAA solution | PEI solution A | CPHEDM solution | A | 52 | 72 | D | 4.3 | — |

TABLE 11-1-continued

|  | Molding subjected to coating | First solution | Second solution | Third solution | Wettability | Dynamic contact angle (Advance) | Friction (gf) | Lubricity | Adhesion of mucin (μg/cm$^2$) | Adhesion of lipid |
|---|---|---|---|---|---|---|---|---|---|---|
| Example 51 | Reference Example 46 | PAA solution | PEI solution A | — | B | — | 61 | D | 3.0 | E |
| Example 52 | Reference Example 46 | PEI solution A | PAA solution | — | A | — | 38 | C | 4.4 | — |
| Example 53 | Reference Example 46 | PEI solution A | CPDA solution A | — | C | — | — | B | — | — |

TABLE 11-2

|  | Molding subjected to coating | First solution | Second solution | Third solution | Wettability | Dynamic contact angle (Advance) | Friction (gf) | Lubricity | Adhesion of mucin (μg/cm$^2$) | Adhesion of lipid |
|---|---|---|---|---|---|---|---|---|---|---|
| Comparative Example 10 | Reference Example 46 | — | — | — | E | 113 | 60 | E | 2.6 | D |
| Comparative Example 11 | Reference Example 46 | PEI solution A | — | — | D | — | — | E | 2.2 | — |
| Comparative Example 12 | Reference Example 46 | PAA solution | — | — | E | — | — | E | 2.3 | — |
| Comparative Example 13 | Reference Example 46 | CPDA solution A | — | — | E | — | — | E | — | — |
| Comparative Example 14 | Reference Example 46 | PVP solution | — | — | E | — | — | E | — | — |
| Comparative Example 15 | Reference Example 46 | VA64 solution | — | — | E | — | — | E | — | — |
| Comparative Example 16 | Reference Example 46 | PDMAA solution | — | — | E | — | — | E | — | — |
| Comparative Example 17 | Reference Example 46 | PEI solution A | PEI solution A | — | C | — | — | E | — | — |
| Comparative Example 18 | Reference Example 46 | PAA solution | PAA solution | — | E | — | — | E | — | — |
| Comparative Example 19 | Reference Example 46 | PAA solution | CPDA solution A | — | E | — | — | E | — | — |
| Comparative Example 20 | Reference Example 46 | AcOH solution | PEI solution A | — | C | — | — | E | — | — |
| Comparative Example 21 | Reference Example 46 | DEA solution | PAA solution | — | E | — | — | E | — | — |
| Comparative Example 22 | Reference Example 46 | AcOH solution | DEA solution | PAA solution | E | — | — | E | — | — |
| Comparative Example 23 | Reference Example 46 | AcOH solution | DEA solution | DEA solution | E | — | — | E | — | — |
| Comparative Example 24 | Reference Example 46 | DEA solution | AcOH solution | AcOH solution | E | — | — | E | — | — |
| Control Example 1 | SHG-A | — | — | — | A | 38 | 38 | B | 2.5 | D |
| Control Example 2 | SHG-B | — | — | — | A | 38 | — | C | 4.6 | A |
| Example 54 | Reference Example 43 | PAA solution | PEI solution A | PAA solution | A | 44 | 46 | C | 2.7 | — |
| Example 55 | Reference Example 43 | PAA solution | PEI solution A | CPDA solution B | A | 32 | 24 | A | 5.4 | — |
| Example 56 | Reference Example 43 | PAA solution | PEI solution A | CPDA solution A | A | 26 | 20 | A | 1.4 | — |
| Example 57 | Reference Example 43 | PAA solution | PEI solution A | CPDA solution C | A | 40 | 35 | A | 1.6 | — |
| Example 58 | Reference Example 43 | PAA solution | PEI solution A | CPVPA solution C | B | 59 | 46 | B | 3.8 | — |
| Example 59 | Reference Example 43 | PAA solution | PEI solution A | CPVPA solution D | B | 60 | 43 | B | 3.4 | — |

SHG-A: Commercially available silicone hydrogel soft contact lens A
SHG-B: Commercially available silicone hydrogel soft contact lens B

TABLE 12

| | Molding subjected to coating | First solution | Second solution | Third solution | Evaluation results | | | |
|---|---|---|---|---|---|---|---|---|
| | | | | | Transparency | Coloration | Wettability | Lubricity |
| Example 60 | Reference Example 44 | PAA solution | PEI solution A | PAA solution | A | — | A | C |
| Example 61 | Reference Example 44 | PAA solution | PEI solution A | CPDA solution B | A | — | A | A |
| Example 62 | Reference Example 44 | PAA solution | PEI solution A | CPDA solution A | A | — | A | A |
| Example 63 | Reference Example 44 | PAA solution | PEI solution A | CPDA solution C | A | — | A | A |
| Example 64 | Reference Example 44 | PAA solution | PEI solution A | CPVPA solution C | A | — | B | B |
| Example 65 | Reference Example 44 | PAA solution | PEI solution A | CPVPA solution D | A | — | B | B |
| Example 66 | Reference Example 45 | PAA solution | PEI solution A | CPDA solution A | A | — | A | A |
| Example 67 | Reference Example 47 | PAA solution | PEI solution A | CPDA solution A | A | — | A | A |
| Example 68 | Reference Example 48 | PAA solution | PEI solution A | CPHA solution A | A | A | B | B |
| Example 69 | Reference Example 49 | PAA solution | PEI solution A | CPHA solution A | A | A | B | B |
| Example 70 | Reference Example 50 | PAA solution | PEI solution A | CPHA solution A | B | A | B | B |
| Example 71 | Reference Example 51 | PAA solution | PEI solution A | CPHA solution A | C | A | B | B |
| Example 72 | Reference Example 52 | PAA solution | PEI solution A | CPHA solution A | A | A | B | B |
| Example 73 | Reference Example 53 | PAA solution | PEI solution A | CPHA solution A | B | A | B | B |
| Example 74 | Reference Example 54 | PAA solution | PEI solution A | CPHA solution A | C | A | B | B |
| Example 75 | Reference Example 55 | PAA solution | PEI solution A | CPHA solution A | A | A | B | B |
| Example 76 | Reference Example 56 | PAA solution | PEI solution A | CPHA solution A | B | A | B | B |
| Example 77 | Reference Example 57 | PAA solution | PEI solution A | CPHA solution A | C | A | B | B |
| Example 78 | Reference Example 58 | PAA solution | PEI solution A | CPHA solution A | A | A | B | B |
| Example 79 | Reference Example 59 | PAA solution | PEI solution A | CPHA solution A | B | A | B | B |
| Example 80 | Reference Example 60 | PAA solution | PEI solution A | CPHA solution A | C | A | B | B |
| Example 81 | Reference Example 61 | PAA solution | PEI solution A | CPHA solution A | A | A | B | B |
| Example 82 | Reference Example 62 | PAA solution | PEI solution A | CPHA solution A | B | A | B | B |
| Example 83 | Reference Example 63 | PAA solution | PEI solution A | CPHA solution A | C | A | B | B |
| Example 84 | Reference Example 64 | PAA solution | PEI solution A | CPHA solution A | A | A | B | B |
| Example 85 | Reference Example 65 | PAA solution | PEI solution A | CPHA solution A | B | A | B | B |
| Example 86 | Reference Example 66 | PAA solution | PEI solution A | CPHA solution A | C | A | B | B |
| Example 87 | Reference Example 67 | PAA solution | PEI solution A | CPHA solution A | A | E | B | B |
| Example 88 | Reference Example 68 | PAA solution | PEI solution A | CPHA solution A | A | E | B | B |
| Example 89 | Reference Example 69 | PAA solution | PEI solution A | CPHA solution A | A | E | B | B |
| Control Example 1 | SHG-A | — | — | — | A | A | A | B |
| Control Example 2 | SHG-B | — | — | — | A | A | A | C |

TABLE 13

| | Molding subjected to coating | First solution | Second solution | Third solution | Fourth solution | Fifth solution |
|---|---|---|---|---|---|---|
| Control Example 1 | SHG-A | — | — | — | — | — |
| Control Example 2 | SHG-B | — | — | — | — | — |

TABLE 13-continued

| | | | | | | | |
|---|---|---|---|---|---|---|---|
| Comparative Example 25 | Reference Example 70 | — | — | — | — | — | — |
| Comparative Example 26 | Reference Example 70 | PAA solution | — | — | — | — | — |
| Comparative Example 27 | Reference Example 70 | PEI solution A | — | — | — | — | — |
| Comparative Example 28 | Reference Example 70 | CPHA solution E | — | — | — | — | — |
| Comparative Example 29 | Reference Example 70 | CPDA solution A | — | — | — | — | — |
| Comparative Example 30 | Reference Example 70 | CPHA solution A | — | — | — | — | — |
| Example 90 | Reference Example 70 | PAA solution | PEI solution A | — | — | — | — |
| Example 91 | Reference Example 70 | PEI solution A | PAA solution | — | — | — | — |
| Example 92 | Reference Example 70 | PAA solution | PEI solution A | PAA solution | — | — | — |
| Example 93 | Reference Example 70 | PAA solution | PEI solution A | CPDA solution A | — | — | — |
| Example 94 | Reference Example 70 | PAA solution | PEI solution A | CPHA solution E | — | — | — |
| Example 95 | Reference Example 70 | CPHA solution E | PEI solution A | CPDA solution A | — | — | — |
| Example 96 | Reference Example 70 | CPDA solution A | PEI solution A | CPHA solution E | — | — | — |
| Example 97 | Reference Example 70 | PAA solution | PEI solution A | *1 | — | — | — |
| Example 98 | Reference Example 70 | PAA solution | PEI solution A | CPHA solution E | PEI solution A | CPDA solution A | — |
| Example 99 | Reference Example 70 | PAA solution | PEI solution A | CPDA solution A | PEI solution A | CPHA solution E | — |
| Example 100 | Reference Example 70 | PAA solution | PEI solution A | CPHA solution A | — | — | — |
| Example 101 | Reference Example 70 | PAA solution | PEI solution A | CPHA solution B | — | — | — |
| Example 102 | Reference Example 70 | PAA solution | PEI solution A | CPHA solution C | — | — | — |
| Example 103 | Reference Example 70 | PAA solution | PEI solution A | CPHA solution F | — | — | — |
| Example 104 | Reference Example 70 | PEI solution A | CPDA solution A | — | — | — | — |
| Example 105 | Reference Example 70 | PAA solution | PEI solution A | CPHA solution A | — | — | — |
| Example 106 | Reference Example 70 | CPDA solution A | PEI solution A | CPHA solution A | — | — | — |
| Example 107 | Reference Example 70 | PAA solution | PEI solution A | *2 | — | — | — |
| Example 108 | Reference Example 70 | PAA solution | PEI solution A | CPHA solution A | PEI solution A | CPDA solution A | — |
| Example 109 | Reference Example 70 | PAA solution | PEI solution A | CPDA solution A | PEI solution A | CPHA solution A | — |

Evaluation results

| | Transparency | Wettability | Lubricity | Adhesion of mucin ($\mu g/cm^2$) | Artificial lacrimal fluid immersion test | Boiling resistance | Scrubbing resistance A | Scrubbing resistance B |
|---|---|---|---|---|---|---|---|---|
| Control Example 1 | A | A | B | 2.5 | B | A | B | B |
| Control Example 2 | A | A | C | 4.6 | E | A | B | B |
| Comparative Example 25 | A | E | E | 3.9 | C | E | E | E |
| Comparative Example 26 | A | D | E | 3.6 | D | E | D | D |
| Comparative Example 27 | A | D | D | 3.1 | E | D | D | D |
| Comparative Example 28 | A | E | E | 3.5 | E | — | — | — |
| Comparative Example 29 | A | E | E | 4.1 | E | E | E | D |
| Comparative Example 30 | A | E | E | 3.9 | D | E | E | E |
| Example 90 | A | B | C | 3.0 | E | B | B | B |
| Example 91 | A | A | C | 8.2 | E | A | A | A |
| Example 92 | A | A | B | 7.5 | E | A | A | A |
| Example 93 | A | A | A | 2.5 | D | A | A | A |
| Example 94 | A | C | C | 2.9 | E | — | — | — |
| Example 95 | A | B | A | 2.4 | E | — | — | — |
| Example 96 | A | C | C | 2.3 | C | — | — | — |
| Example 97 | A | B | A | 3.1 | C | — | — | — |
| Example 98 | A | B | A | 2.9 | C | — | — | — |
| Example 99 | A | C | C | 3.0 | D | — | — | — |
| Example 100 | A | B | B | 2.3 | C | B | B | B |
| Example 101 | A | B | B | 2.8 | C | — | — | — |
| Example 102 | A | C | B | 3.7 | C | — | — | — |
| Example 103 | A | C | B | 2.3 | C | — | — | — |
| Example 104 | A | B | A | 2.5 | E | B | B | B |
| Example 105 | A | B | B | 2.9 | C | B | B | B |
| Example 106 | A | C | B | 2.6 | C | C | C | C |
| Example 107 | A | C | A | 3.3 | C | C | C | C |
| Example 108 | A | B | A | 3.2 | C | B | B | B |
| Example 109 | A | C | B | 2.4 | C | C | C | C |

*1: 1:1 (weight) mixture OF CPHA solution E and CPDA solution A
*2: 1:1 (weight) mixture of CPHA solution A and CPDA solution A

TABLE 14

|  | Molding subjected to coating | First solution | Second solution | Third solution |
|---|---|---|---|---|
| Control Example 1 | SHG-A | — | — | — |
| Control Example 2 | SHG-B | — | — | — |
| Example 110 | Reference Example 72 | PAA solution | PEI solution A | CPHA solution A |
| Example 111 | Reference Example 73 | PAA solution | PEI solution A | CPHA solution A |
| Example 112 | Reference Example 74 | PAA solution | PEI solution A | CPHA solution A |
| Example 113 | Reference Example 75 | PAA solution | PEI solution A | CPHA solution A |

| | Evaluation results | | | | | |
|---|---|---|---|---|---|---|
| | Transparency | Transparency (Projector) | Water content (%) | Lens molding ratio | Tensile elastic modulus (kPa) | Elongation at break (%) |
| Control Example 1 | A | A | 19 | — | 2000 | 240 |
| Control Example 2 | A | A | 37 | — | 850 | 240 |
| Example 110 | A | B | Less than 1 | 0.917 | 660 | 410 |
| Example 111 | A | B | Less than 1 | 0.916 | 740 | 320 |
| Example 112 | A | A | Less than 1 | 0.939 | 880 | 390 |
| Example 113 | A | C | Less than 1 | 0.905 | 630 | 300 |

| | Evaluation results | | | | |
|---|---|---|---|---|---|
| | Wettability | Lubricity | Boiling resistance | Scrubbing resistance A | Scrubbing resistance B |
| Control Example 1 | A | C | A | B | B |
| Control Example 2 | A | B | A | B | B |
| Example 110 | B | B | B | B | B |
| Example 111 | B | B | B | B | B |
| Example 112 | B | B | B | B | B |
| Example 113 | B | B | B | B | B |

TABLE 15

| | Molding subjected to coating | First solution | Second solution | Third solution | Evaluation results | | | |
|---|---|---|---|---|---|---|---|---|
| | | | | | Transparency | Folding resistance | Wettability | Lubricity |
| Control Example 1 | SHG-A | — | — | — | A | A | A | C |
| Control Example 2 | SHG-B | — | — | — | A | A | A | B |
| Example 114 | Reference Example 1 | PAA solution | PEI solution A | CPHA solution A | A | A | B | B |
| Example 115 | Reference Example 2 | PAA solution | PEI solution A | CPHA solution A | A | A | B | B |
| Example 116 | Reference Example 3 | PAA solution | PEI solution A | CPHA solution A | A | A | B | B |
| Example 117 | Reference Example 4 | PAA solution | PEI solution A | CPHA solution A | A | A | B | B |
| Example 118 | Reference Example 5 | PAA solution | PEI solution A | CPHA solution A | B | A | B | B |
| Example 119 | Reference Example 6 | PAA solution | PEI solution A | CPHA solution A | C | A | B | B |
| Example 120 | Reference Example 7 | PAA solution | PEI solution A | CPHA solution A | C | A | B | B |
| Example 121 | Reference Example 8 | PAA solution | PEI solution A | CPHA solution A | C | A | B | B |
| Example 122 | Reference Example 9 | PAA solution | PEI solution A | CPHA solution A | C | A | B | B |
| Example 123 | Reference Example 10 | PAA solution | PEI solution A | CPHA solution A | C | A | B | B |
| Example 124 | Reference Example 11 | PAA solution | PEI solution A | CPHA solution A | D | A | B | B |
| Example 125 | Reference Example 13 | PAA solution | PEI solution A | CPHA solution A | C | B | B | B |
| Example 126 | Reference Example 14 | PAA solution | PEI solution A | CPHA solution A | A | B | B | B |
| Example 127 | Reference Example 15 | PAA solution | PEI solution A | CPHA solution A | A | B | B | B |
| Example 128 | Reference Example 16 | PAA solution | PEI solution A | CPHA solution A | A | C | B | B |

TABLE 15-continued

| | Molding subjected to coating | First solution | Second solution | Third solution | Evaluation results | | | |
|---|---|---|---|---|---|---|---|---|
| | | | | | Transparency | Folding resistance | Wettability | Lubricity |
| Example 129 | Reference Example 17 | PAA solution | PEI solution A | CPHA solution A | A | E | B | B |
| Example 130 | Reference Example 18 | PAA solution | PEI solution A | CPHA solution A | A | E | B | B |
| Example 131 | Reference Example 19 | PAA solution | PEI solution A | CPHA solution A | A | E | B | B |
| Example 132 | Reference Example 20 | PAA solution | PEI solution A | CPHA solution A | A | D | B | B |
| Example 133 | Reference Example 21 | PAA solution | PEI solution A | CPHA solution A | B | E | B | B |
| Example 134 | Reference Example 22 | PAA solution | PEI solution A | CPHA solution A | A | D | B | B |
| Example 135 | Reference Example 24 | PAA solution | PEI solution A | CPHA solution A | A | D | B | B |
| Example 136 | Reference Example 25 | PAA solution | PEI solution A | CPHA solution A | A | E | B | B |
| Example 137 | Reference Example 26 | PAA solution | PEI solution A | CPHA solution A | A | D | B | B |
| Example 138 | Reference Example 27 | PAA solution | PEI solution A | CPHA solution A | B | D | B | B |
| Example 139 | Reference Example 28 | PAA solution | PEI solution A | CPHA solution A | E | E | B | B |
| Example 140 | Reference Example 29 | PAA solution | PEI solution A | CPHA solution A | D | D | B | B |
| Example 141 | Reference Example 30 | PAA solution | PEI solution A | CPHA solution A | D | D | B | B |
| Example 142 | Reference Example 31 | PAA solution | PEI solution A | CPHA solution A | B | D | B | B |
| Example 143 | Reference Example 32 | PAA solution | PEI solution A | CPHA solution A | B | A | B | B |
| Example 144 | Reference Example 33 | PAA solution | PEI solution A | CPHA solution A | B | A | B | B |
| Example 145 | Reference Example 34 | PAA solution | PEI solution A | CPHA solution A | A | A | B | B |
| Example 146 | Reference Example 35 | PAA solution | PEI solution A | CPHA solution A | A | A | B | B |
| Example 147 | Reference Example 36 | PAA solution | PEI solution A | CPHA solution A | B | A | B | B |
| Example 148 | Reference Example 37 | PAA solution | PEI solution A | CPHA solution A | D | B | B | B |

TABLE 16

| | Molding subjected to coating | First solution | Second solution | Third solution | Evaluation results | | | |
|---|---|---|---|---|---|---|---|---|
| | | | | | Transparency | Folding resistance | Wettability | Lubricity |
| Example 149 | Reference Example 1 | PAA solution | PEI solution A | CPDA solution A | A | A | A | A |
| Example 150 | Reference Example 2 | PAA solution | PEI solution A | CPDA solution A | A | A | A | A |
| Example 151 | Reference Example 3 | PAA solution | PEI solution A | CPDA solution A | A | A | A | A |
| Example 152 | Reference Example 4 | PAA solution | PEI solution A | CPDA solution A | A | A | A | A |
| Example 153 | Reference Example 5 | PAA solution | PEI solution A | CPDA solution A | B | A | A | A |
| Example 154 | Reference Example 6 | PAA solution | PEI solution A | CPDA solution A | C | A | A | A |
| Example 155 | Reference Example 7 | PAA solution | PEI solution A | CPDA solution A | C | A | A | A |
| Example 156 | Reference Example 8 | PAA solution | PEI solution A | CPDA solution A | C | A | A | A |
| Example 157 | Reference Example 9 | PAA solution | PEI solution A | CPDA solution A | C | A | A | A |
| Example 158 | Reference Example 10 | PAA solution | PEI solution A | CPDA solution A | C | A | A | A |
| Example 159 | Reference Example 11 | PAA solution | PEI solution A | CPDA solution A | D | A | A | A |
| Example 160 | Reference Example 13 | PAA solution | PEI solution A | CPDA solution A | C | B | A | A |

TABLE 16-continued

| | Molding subjected to coating | First solution | Second solution | Third solution | Evaluation results | | | |
|---|---|---|---|---|---|---|---|---|
| | | | | | Transparency | Folding resistance | Wettability | Lubricity |
| Example 161 | Reference Example 14 | PAA solution | PEI solution A | CPDA solution A | A | B | A | A |
| Example 162 | Reference Example 15 | PAA solution | PEI solution A | CPDA solution A | A | B | A | A |
| Example 163 | Reference Example 16 | PAA solution | PEI solution A | CPDA solution A | A | C | A | A |
| Example 164 | Reference Example 17 | PAA solution | PEI solution A | CPDA solution A | A | E | A | A |
| Example 165 | Reference Example 18 | PAA solution | PEI solution A | CPDA solution A | A | E | A | A |
| Example 166 | Reference Example 19 | PAA solution | PEI solution A | CPDA solution A | A | E | A | A |
| Example 167 | Reference Example 20 | PAA solution | PEI solution A | CPDA solution A | A | D | A | A |
| Example 168 | Reference Example 21 | PAA solution | PEI solution A | CPDA solution A | B | E | A | A |
| Example 169 | Reference Example 22 | PAA solution | PEI solution A | CPDA solution A | A | D | A | A |
| Example 170 | Reference Example 24 | PAA solution | PEI solution A | CPDA solution A | A | D | A | A |
| Example 171 | Reference Example 25 | PAA solution | PEI solution A | CPDA solution A | A | E | A | A |
| Example 172 | Reference Example 26 | PAA solution | PEI solution A | CPDA solution A | A | D | A | A |
| Example 173 | Reference Example 27 | PAA solution | PEI solution A | CPDA solution A | B | D | A | A |
| Example 174 | Reference Example 28 | PAA solution | PEI solution A | CPDA solution A | E | E | A | A |
| Example 175 | Reference Example 29 | PAA solution | PEI solution A | CPDA solution A | D | D | A | A |
| Example 176 | Reference Example 30 | PAA solution | PEI solution A | CPDA solution A | D | D | A | A |
| Example 177 | Reference Example 31 | PAA solution | PEI solution A | CPDA solution A | B | D | A | A |
| Example 178 | Reference Example 32 | PAA solution | PEI solution A | CPDA solution A | B | A | A | A |
| Example 179 | Reference Example 33 | PAA solution | PEI solution A | CPDA solution A | B | A | A | A |
| Example 180 | Reference Example 34 | PAA solution | PEI solution A | CPDA solution A | A | A | A | A |
| Example 181 | Reference Example 35 | PAA solution | PEI solution A | CPDA solution A | A | A | A | A |
| Example 182 | Reference Example 36 | PAA solution | PEI solution A | CPDA solution A | B | A | A | A |
| Example 183 | Reference Example 37 | PAA solution | PEI solution A | CPDA solution A | D | B | A | A |

Example 184

Measurement of Oxygen Transmission Rate

A film (having a thickness of 0.19 mm) produced in the same manner as in Example 62 was cut into size of 20 mm×20 mm, to obtain samples. Using an oxygen transmission rate analyzer, Model OX-TRAN2/21 (Hitachi High-Technologies Corporation), oxygen transmission rate was measured. A mixed gas of nitrogen (98%)/hydrogen (2%) was used as a carrier gas, and a mixed gas of nitrogen (79.3%)/oxygen (20.7%) was used as a measuring gas. Humidification of the gas was not carried out. The oxygen transmission rate of the sample was $390 \times 10^{-11}$ $(cm^2/sec)$ $(mLO_2)/(mL \cdot hPa)$. The oxygen transmission rate of a gas permeable hard contact lens "Menicon® Z" manufactured by Menicon Co., Ltd., measured by the same apparatus under the same conditions, was $150 \times 10^{11}$ $(cm^2/sec)$ $(mLO_2)/(mL \cdot hPa)$, and the oxygen transmission rate of a gas permeable hard contact lens "Breath-o Hard" manufactured by Toray Industries, Inc. was $120 \times 10^{-11}$ $(cm^2/sec)$ $(mLO_2)/(mL \cdot hPa)$.

Example 185

Subjects A and B wore the low water content soft contact lens produced in Example 93 for 6 hours. Both subjects A and B did not feel dry during wear, and felt comfort without feeling sticky to the cornea.

Example 186

Subjects A and B wore the low water content soft contact lens produced in Example 100 for 6 hours. Both subjects A and B did not feel dry during wear, and felt comfort without feeling sticky to the cornea.

Comparative Example 31

Subjects A and B wore a commercially available silicone hydrogel soft contact lens C (water content: 46%) for 6 hours. Both subjects A and B felt dryness of eyes and did not feel comfort. They did not feel sticky to the cornea.

Comparative Example 32

A contact lens produced in accordance with Example 6 of Japanese Unexamined Patent Publication (Kokai) No. 2002-080538 was subjected to the same coating operation as in Example 93. The obtained silicone hydrogel soft contact lens (having water content of 40%) exhibits transparency (A), wettability (A) and lubricity (A). Subjects A and B wore the silicone hydrogel soft contact lens for 6 hours. Both subjects A and B felt dryness of eyes and did not feel comfort. They did not feel sticky to the cornea.

Comparative Example 33

Subjects A and B wore a low water content soft contact lens (having water content of less than 1%) in accordance with Example 1 of Japanese Unexamined Patent Publication (Kokai) No. 2002-311395. Both subjects A and B felt sticky to the cornea within 30 minutes and stopped wearing.

The present invention relates to a low water content soft lens for eye, and is useful as a lens for eye, such as a low water content soft contact lens, an intraocular lens, an artificial cornea, a corneal inlay, a corneal onlay or a spectacle lens. The low water content soft lens for eye is particularly suitable as a low water content soft contact lens.

REFERENCE SIGNS LIST

1: Artificial leather
2: Sample film
3: Rubber plate
4: Plastic container containing iron balls

The invention claimed is:

1. A low water content soft lens for eye, comprising a base material, a layer made of an acidic polymer and a basic polymer being formed on at least a part of a surface of the base material,
    wherein the water content of the lens is 1% or less;
    wherein the layer made of an acidic polymer and a basic polymer is composed of one layer made of an acidic polymer and one layer made of a basic polymer, so two layers in total; or the layer made of an acidic polymer and a basic polymer is composed of one or two layers made of an acidic polymer, and one or two layers made of a basic polymer, and three layers in total;
    wherein the base material contain, as a main component, a polymer of the following component A, or a copolymer of the following components A and B:
        component A: a polysiloxane compound which has a plurality of polymerizable functional groups per molecule, and also has a number average molecular weight of 6,000 or more, and
        component B: a polymerizable monomer having a fluoroalkyl group;
    the component A is a polysiloxane compound represented by the following formula (A1):

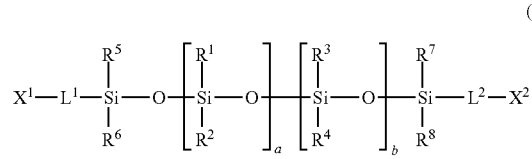

(A1)

wherein $X^1$ and $X^2$ each independently represents a polymerizable functional group; $R^1$ to $R^8$ each independently represents a substituent selected from hydrogen, an alkyl group having 1 to 20 carbon atoms, a phenyl group and a fluoroalkyl group having 1 to 20 carbon atoms; $L^1$ and $L^2$ each independently represents a divalent group; and a and b each independently represents the number of the respective repeating units, and $X^1$ and $X^2$ in the formula (A1) are (meth)acryloyl groups,
    the layer made of an acidic polymer and a basic polymer contains two or more kinds of acidic polymers and one or more kinds of basic polymers.

2. The low water content soft lens for eye according to claim 1, wherein the base material contains 5% by weight or more of silicon atoms.

3. The low water content soft lens for eye according to claim 1, wherein the component B is a (meth)acrylic acid fluoroalkyl ester.

4. The low water content soft lens for eye according to claim 1, wherein at least one kind among the acidic and basic polymers is a polymer having a group selected from a hydroxyl group and an amide bond.

5. The low water content soft lens for eye according to claim 4, wherein at least one kind among the acidic and basic polymers is a polymer having a hydroxyl group.

6. The low water content soft lens for eye according to claim 1, wherein L1 and L2 are divalent groups having 1 to 20 carbon atoms represented by the following formulas (LE1) or (LE3):

OCH2CH2CH2 (LE1)

OCH2CH2NHCOOCH2CH2CH2 (LE3).

7. A low water content soft lens for eye, comprising a base material, a layer made of an acidic polymer and a basic polymer being formed on at least a part of a surface of the base material, wherein the water content of the lens is 1% or less;
    wherein the layer made of an acidic polymer and a basic polymer is composed of one layer made of an acidic polymer and one layer made of a basic polymer, so two layers in total; or the layer made of an acidic polymer and a basic polymer is composed of one or two layers made of an acidic polymer, and one or two layers made of a basic polymer, and three layers in total;
    wherein the base material contain, as a main component, a polymer of the following component A, or a copolymer of the following components A and B:
        component A: a polysiloxane compound which has a plurality of polymerizable functional groups per molecule, and also has a number of average molecular weight of 6,000 or more, and
        component B: a polymerizable monomer having a fluoroalkyl group;
    the component A is a polysiloxane compound represented by the following formula (A1):

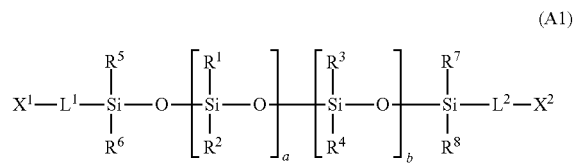

(A1)

wherein $X^1$ and $X^2$ each independently represents a polymerizable functional group; $R^1$ to $R^8$ each independently represents a substituent selected from hydrogen, an alkyl group having 1 to 20 carbon atoms, a phenyl group and a fluoroalkyl group having 1 to 20 carbon atoms; $L^1$ and $L^2$ each independently represents a divalent group; and a and b each independently represents the number of the respective repeating units, and $X^1$ and $X^2$ in the formula (A1) are (meth)acryloyl groups; and wherein two or more kinds among the acidic and basic polymers are polymers having a group selected from a hydroxyl group and an amide bond.

8. The low water content soft lens for eye according to claim 7, wherein the base material contains 5% by weight or more of silicon atoms.

9. The low water content soft lens for eye according to claim 7, wherein the component B is a (meth)acrylic acid fluoroalkyl ester.

10. The low water content soft lens for eye according to claim 7, wherein at least one kind among the acidic and basic polymers is a polymer having a hydroxyl group.

11. The low water content soft lens for eye according to claim 7, wherein $L^1$ and $L^2$ are divalent groups having 1 to 20 carbon atoms represented by the following formulas (LE1) or (LE3):

OCH$_2$CH$_2$CH$_2$     (LE1)

OCH$_2$CH$_2$NHCOOCH$_2$CH$_2$CH$_2$     (LE3).

12. A low water content soft lens for eye, comprising a base material, a layer made of an acidic polymer and a basic polymer being formed on at least a part of a surface of the base material, wherein the water content of the lens is 1% or less;

wherein the layer made of an acidic polymer and a basic polymer is composed of one layer made of an acidic polymer and one layer made of a basic polymer, so two layers in total; or the layer made of an acidic polymer and a basic polymer is composed of one or two layers made of an acidic polymer, and one or two layers made of a basic polymer, and three layers in total;

wherein the base material contain, as a main component, a polymer of the following component A, or a copolymer of the following components A and B:

component A: a polysiloxane compound which has a plurality of polymerizable functional groups per molecule, and also has a number of average molecular weight of 6,000 or more, and component B: a polymerizable monomer having a fluoroalkyl group;

the component A is a polysiloxane compound represented by the following formula (A1):

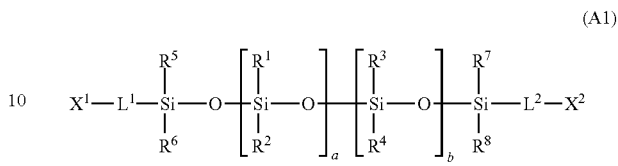

(A1)

wherein $X^1$ and $X^2$ each independently represents a polymerizable functional group; $R^1$ to $R^8$ each independently represents a substituent selected from hydrogen, an alkyl group having 1 to 20 carbon atoms, a phenyl group and a fluoroalkyl group having 1 to 20 carbon atoms; $L^1$ and $L^2$ each independently represents a divalent group; and a and b each independently represents the number of the respective repeating units, and $X^1$ and $X^2$ in the formula (A1) are (meth)acryloyl groups; and, wherein the acidic polymer comprises a polymer having a group selected from an amide bond and a hydroxyl group.

13. The low water content soft lens for eye according to claim 12, wherein the base material contains 5% by weight or more of silicon atoms.

14. The low water content soft lens for eye according to claim 12, wherein the component B is a (meth)acrylic acid fluoroalkyl ester.

15. The low water content soft lens for eye according to claim 12, wherein at least one kind among the acidic and basic polymers is a polymer having a hydroxyl group.

16. The low water content soft lens for eye according to claim 12, wherein $L^1$ and $L^2$ are divalent groups having 1 to 20 carbon atoms represented by the following formulas (LE1) or (LE3):

OCH$_2$CH$_2$CH$_2$     (LE1)

OCH$_2$CH$_2$NHCOOCH$_2$CH$_2$CH$_2$     (LE3).

\* \* \* \* \*